US011013786B2

(12) United States Patent
Svanborg et al.

(10) Patent No.: US 11,013,786 B2
(45) Date of Patent: May 25, 2021

(54) THERAPY

(71) Applicant: SELECTIMMUNE PHARMA AB, Lund (SE)

(72) Inventors: Catharina Svanborg, Malmo (SE); Ines Ambite, Lund (SE)

(73) Assignee: SelectImmune Pharma AB, Lund (SE)

( * ) Notice: Subject to any disclaimer, the term of this patent is extended or adjusted under 35 U.S.C. 154(b) by 379 days.

(21) Appl. No.: 15/542,041

(22) PCT Filed: Jan. 7, 2016

(86) PCT No.: PCT/IB2016/050070
§ 371 (c)(1),
(2) Date: Jul. 6, 2017

(87) PCT Pub. No.: WO2016/110818
PCT Pub. Date: Jul. 14, 2016

(65) Prior Publication Data
US 2018/0125939 A1 May 10, 2018

Related U.S. Application Data

(60) Provisional application No. 62/101,110, filed on Jan. 8, 2015.

(51) Int. Cl.
A61K 38/20 (2006.01)
A61K 38/17 (2006.01)
G01N 33/68 (2006.01)
C12Q 1/6883 (2018.01)
C12Q 1/68 (2018.01)
A61P 13/02 (2006.01)
A61K 31/381 (2006.01)
G01N 33/573 (2006.01)

(52) U.S. Cl.
CPC ........ A61K 38/2006 (2013.01); A61K 31/381 (2013.01); A61K 38/17 (2013.01); A61P 13/02 (2018.01); C12Q 1/68 (2013.01); C12Q 1/6883 (2013.01); C12Y 304/24023 (2013.01); G01N 33/573 (2013.01); G01N 33/6869 (2013.01); G01N 33/6893 (2013.01); C12Q 2600/106 (2013.01); C12Q 2600/118 (2013.01); C12Q 2600/156 (2013.01); C12Q 2600/158 (2013.01); G01N 2333/545 (2013.01); G01N 2333/96494 (2013.01); G01N 2800/348 (2013.01); G01N 2800/50 (2013.01)

(58) Field of Classification Search
None
See application file for complete search history.

(56) References Cited

U.S. PATENT DOCUMENTS

| 4,244,968 A | 1/1981 | Friedmann |
| 5,075,222 A | 12/1991 | Hannum et al. |
| 6,289,236 B1 * | 9/2001 | Koenig ................ A61B 1/043 600/477 |
| 2011/0144002 A1 | 6/2011 | Ravn et al. |

FOREIGN PATENT DOCUMENTS

| EP | 1 880 719 A2 | 1/2008 |
| WO | WO-2006136004 A1 * | 12/2006 ........... A61K 31/675 |
| WO | 2016/110818 A2 | 7/2016 |

OTHER PUBLICATIONS

Dinarello et.al. Semin Immunol. Dec. 15, 2013; 25(6): 469-484. doi:10.1016/j.smim.2013.10.008 (Year: 2013).*
Martins et al., J.of Urology, vol. 151, pp. 1198-1201 (Year: 1994).*
Rafalsky et al.,Cochrane Database of Systemic Reviews No. 3, Art No. CD003597, pp. 1-54 (Year: 2006).*
Dinarello (2011, Blood, vol. 117(14), pp. 3720-3732)i (Year: 2011).*
Durrant et al., "Pyrone-Based Inhibitors of Metalloproteinase Types 2 and 3 May Work as Conformation-Selective Inhibitors", Chem Biol Drug Des, 2011, pp. 191-198, vol. 78.
Freigang et al., "Fatty acid-induced mitochondrial uncoupling elicits inflammasome-independent IL-1α and sterile vascular inflammation in atherosclerosis", Nature Immunology, 2013, pp. 1045-1053, vol. 14, No. 10.
Hedges et al., "The mucosal cytokine response to urinary tract infections", International Journal of Antimicrobial Agents, 1994, pp. 89-93, vol. 4.
Horai et al., "Production of Mice Deficient in Genes for Interleukin (IL)-1α, IL-1β, IL-1α/β, and IL-1 Receptor Antagonist Shows that IL-1β Is Crucial in Turpentine-induced Fever Development and Glucocorticoid Secretion", Journal of Experimental Medicine, 1998, pp. 1463-1475, vol. 187, No. 9.
Hoshino et al., "Cutting Edge: Toll-Like Receptor 4 (TLR4)-Deficient Mice Are Hyporesponsive to Lipopolysaccharide: Evidence for TLR4 as the Lps Gene Product", The Journal of Immunology, 1999, pp. 3749-3752, vol. 162.
International Search Report and Written Opinion from International Application No. PCT/IB2016/050070, dated Jul. 6, 2016; 16 pgs.
Kayagaki et al., "Non-canonical inflammasome activation targets caspase-11", Nature, 2011, pp. 117-121, vol. 479.
Kjolvmark et al., "Heparin-Binding Protein: A Diagnostic Biomarker of Urinary Tract Infection in Adults", Open Forum Infectious Diseases, 2014, pp. 1-9, vol. 1, No. 1.
Lindberg et al., "Asymptomatic bacteriuria in schoolgirls", The Journal of Pediatrics, 1978, pp. 194-199, vol. 92, No. 1.
Mariathasan et al., "Differential activation of the inflammasome by caspase-1 adaptors ASC and Ipaf", Nature, 2004, pp. 213-218, vol. 430.

(Continued)

Primary Examiner — Gary B Nickol
Assistant Examiner — Jegatheesan Seharaseyon

(57) ABSTRACT

A method for treating cystitis, in particular acute cystitis, comprising administering to a patient in need thereof, an effective amount of a reagent selected from the group consisting of IL-1β inhibitors and MMP inhibitors, or proteins selected from ASC or NLRP-3. Diagnostic methods are also described and claimed.

Figure 1A:
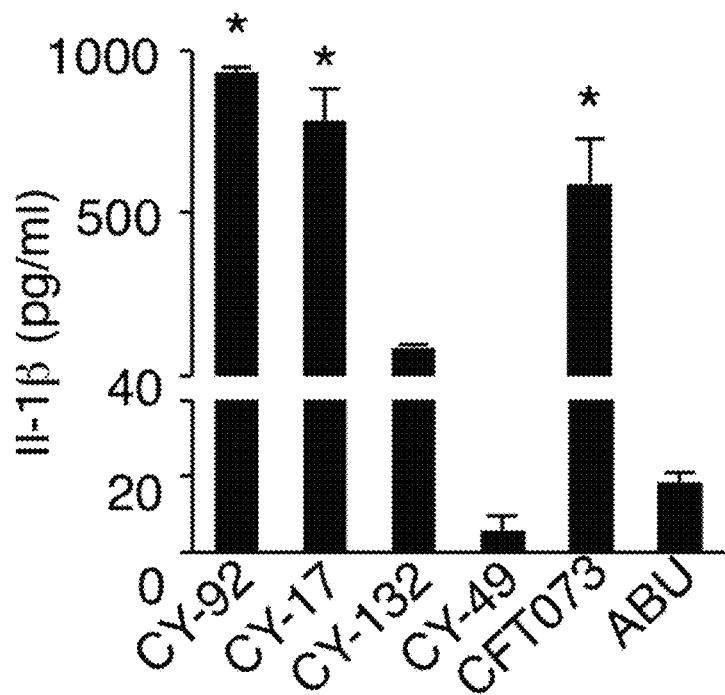

7 Claims, 21 Drawing Sheets
(16 of 21 Drawing Sheet(s) Filed in Color)

(56) References Cited

OTHER PUBLICATIONS

Mariathasan et al., "Cryopyrin activates the inflammasome in response to toxins and ATP", Nature, 2006, pp. 228-232, vol. 440.
Nielubowicz et al., "Host-pathogen interactions in urinary tract infection", Nature Reviews Urology, 2010, pp. 430-441, vol. 7.
Sato et al., "Distinct and Essential Roles of Transcription Factors IRF-3 and IRF-7 in Response to Viruses for IFN-α/β Gene Induction", Immunity, 2000, pp. 539-548, vol. 13.
Sheu et al., "Urine interleukin-1β in children with acute pyelonephritis and renal scarring", Nephrology, 2007, pp. 487-493, vol. 12, No. 5.
Sivick et al., "Waging War against Uropathogenic *Escherichia coli*: Winning Back the Urinary Tract", Infection and Immunity, 2010, pp. 568-585, vol. 78, No. 2.
Sunden et al., "*Escherichia coli* 83972 Bacteriuria Protects Against Recurrent Lower Urinary Tract Infections in Patients With Incomplete Bladder Emptying", The Journal of Urology, 2010, pp. 179-185, vol. 184.
Wilson et al., "Intestinal tumorigenesis is suppressed in mice lacking the metalloproteinase matrilysin", PNAS, 1997, pp. 1402-1407, vol. 94.
Kafka et al., "Contribution of IL-1 to resistance to *Streptococcus pneumoniae* infection", International Immunology, 2008, pp. 1139-1146, vol. 20, No. 9.
Vonk et al., "Endogenous Interleukin (IL)-1α and IL-1β Are Crucial for Host Defense against Disseminated Candidiasis", The Journal of Infectious Diseases, 2006, pp. 1419-1426, vol. 193.
Zwijnenburg et al., "IL-1 Receptor Type 1 Gene-Deficient Mice Demonstrate an Impaired Host Defense Against Pneumococcal Meningitis", The Journal of Immunology, 2003, pp. 4724-4730, vol. 170.
Konstantinopoulos et al., "Matrix metalloproteinase inhibitors as anticancer agents", The International Journal of Biochemistry & Cell Biology, 2008, pp. 1156-1168, vol. 40.

\* cited by examiner

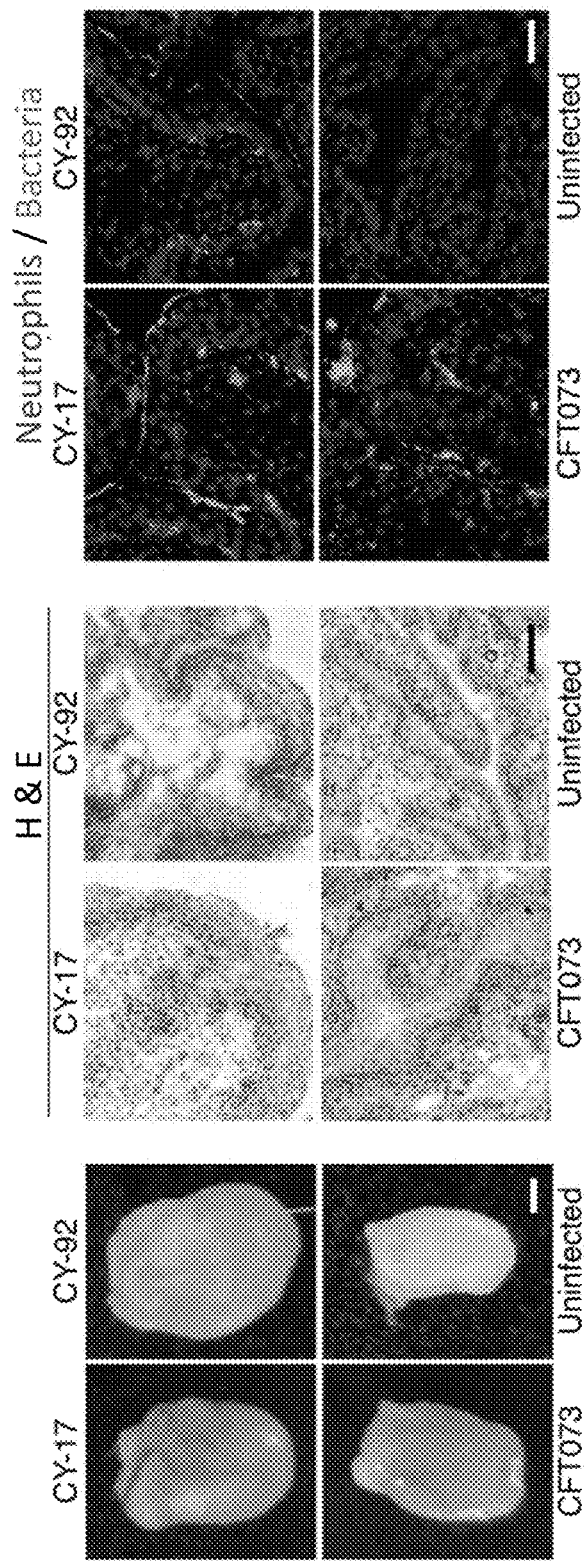
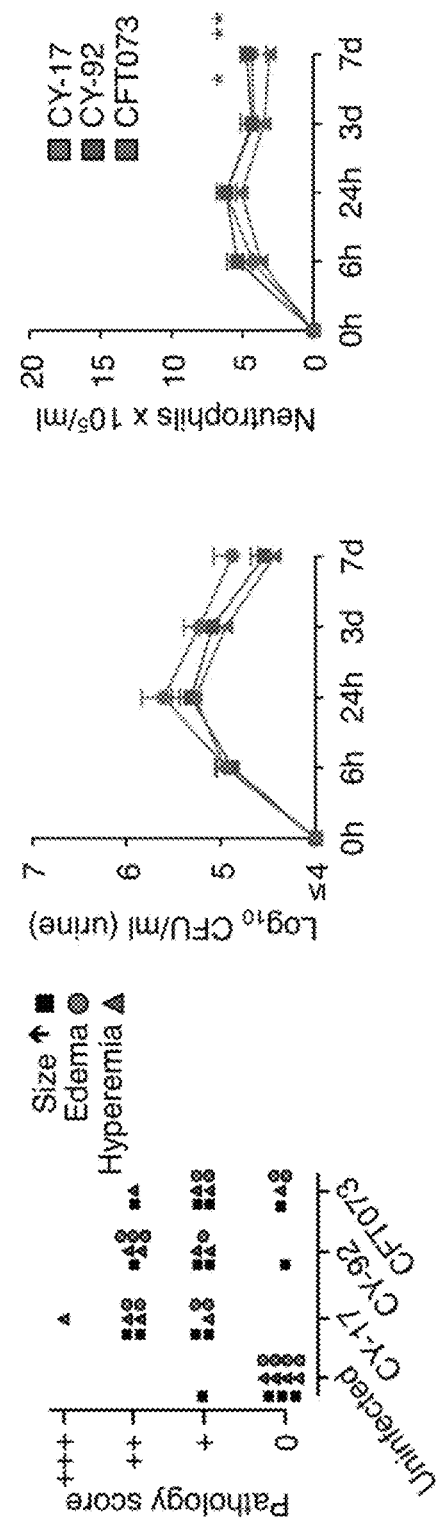
FIG. 2A
FIG. 2B

FIG. 3D

| Symbol | Gene Name | Asc-/-,1 | Asc-/-,2 | Nlrp3-/-,1 | Asc-/-,3 |
|---|---|---|---|---|---|
| *Mmp7* | matrix metallopeptidase 7 | 240 | 124 | 259 | 114 |
| *Cxcl6* | chemokine (C-X-C motif) ligand 6 | 95 | 240 | 232 | 381 |
| *Stfa1* | stefin A1 (cysteinase inhibitor) | 85 | 23 | 94 | 69 |
| *Aqp4* | aquaporin 4 | 79.7 | 17 | 56 | 34 |
| *Cxcl3* | chemokine (C-X-C motif) ligand 3 (GRO-γ) | 73 | 198 | 137 | 231 |
| *Ltf* | lactotransferrin | 72 | 33 | 87 | 66 |
| *S100a8* | S100 calcium binding protein A8 | 57 | 90 | 125 | 107 |
| *Gabrp* | (GABA) A receptor, pi | 49 | 17 | 31 | 19 |
| *Fam3b* | family with sequence similarity 3, member B | 35 | 26 | 22 | 35 |
| *Ifit1* | IFN-induced protein with tetratricopeptide repeats 1 | 34 | 72 | 110 | |
| *Olfm4* | olfactomedin 4 | 34 | 11 | 32 | 46 |
| *S100a9* | S100 calcium binding protein A9 | 26 | 36 | 47 | 59 |
| *Tnfrsf11b* | TNF receptor superfamily, member 11b | 22 | 31 | 33 | 9 |

FIG. 4A

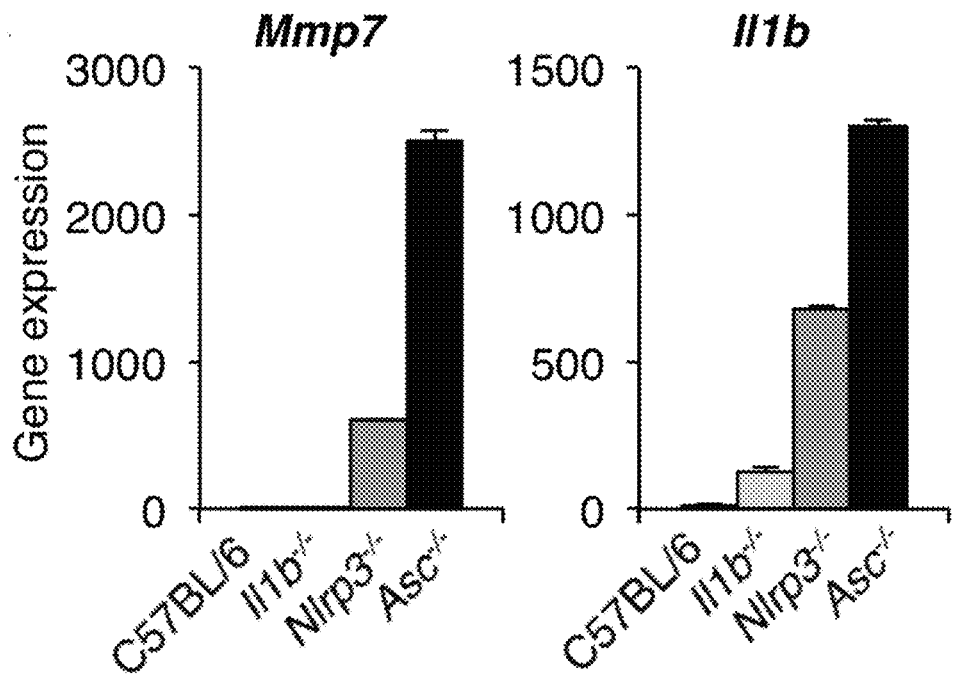

FIG. 4B

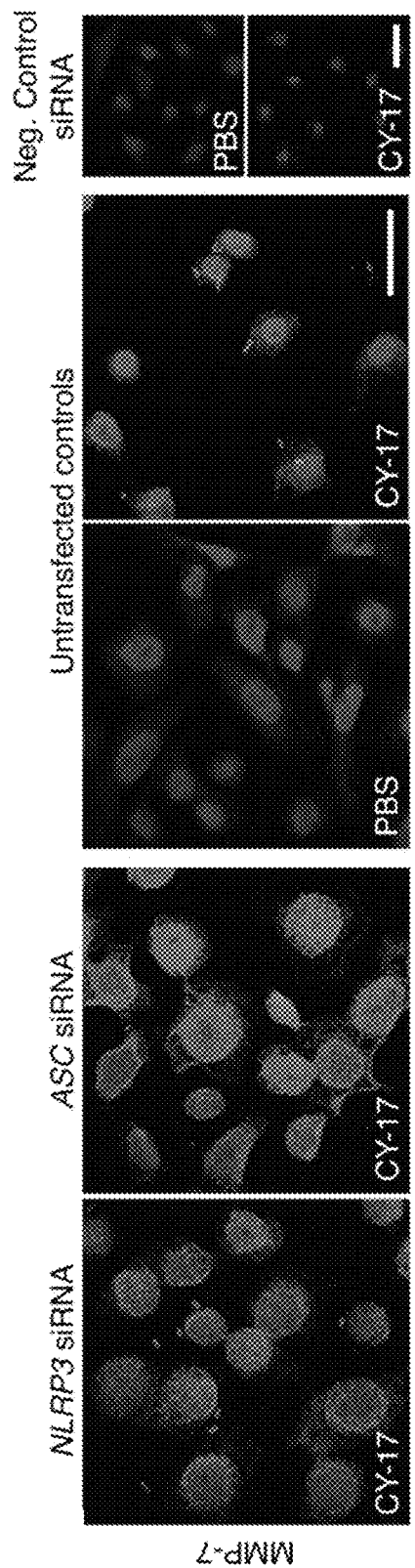
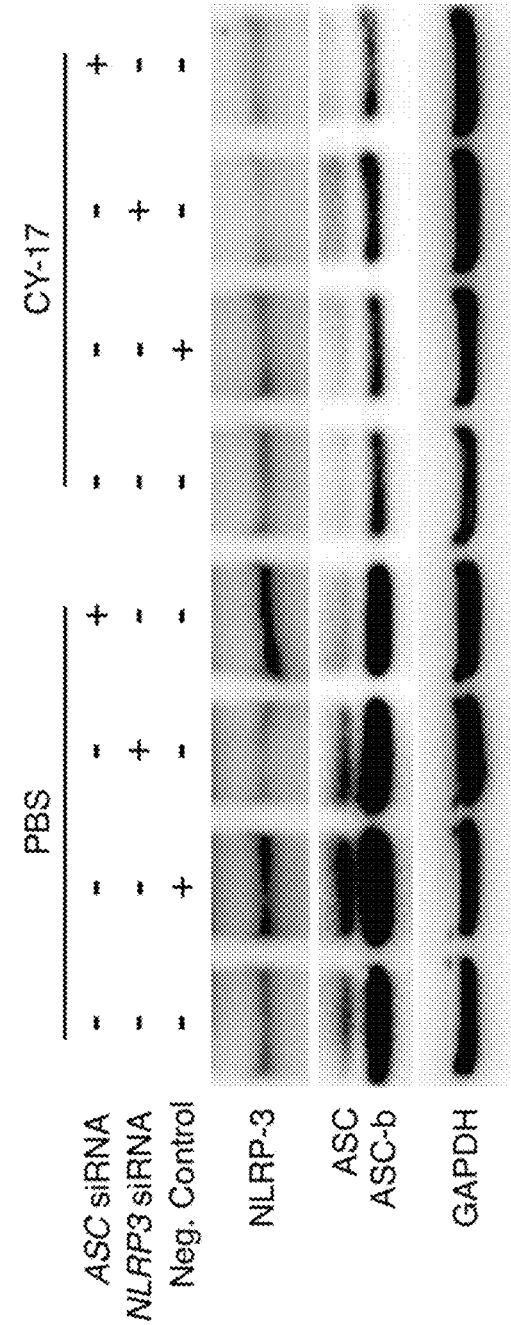
FIG. 5A
FIG. 5B

THERAPY

The present invention relates to methods for treating cystitis and in particular acute cystitis, to compositions for use in these therapies.

BACKGROUND OF THE INVENTION

Urinary tract infections (UTIs) are common and may be dangerous. The clinical presentation and severity varies, depending on the site of infection and molecular basis of disease. In acute pyelonephritis (APN), bacteria ascend into the renal pelvis, where they cause an intense mucosal inflammatory response with progression into the renal parenchyma. Symptoms include high fever, malaise, loin pain as well as poor feeding and irritability in infants. In acute cystitis, infection is localized to the urinary bladder, resulting in dysuria, frequency and supra-pubic pain, typically without systemic involvement. While the clinical entities of acute pyelonephritis and acute cystitis typically are quite distinct, the molecular determinants of clinical presentation and severity are largely unknown.

In acute pyelonephritis, a pathogen-specific TLR4 response is activated by P fimbriated $E.\ coli$, through ceramide release and the successive phosphorylation of the TICAM-1 (TRIF) and TICAM-2 (TRAM) adaptors, CREB-1, c-FOS and c-JUN activates IRF- and AP1-dependent transcription. Additional involvement of MyD88, TIRAP and NF-kB depends on the virulence repertoire of the infecting strain. Genetic studies in the murine UTI model have identified IRF3-dependent gene expression and mCXCR2-dependent neutrophil activation as determinants of bacterial clearance and tissue homeostasis. Infected $Irf3^{-/-}$ or $mCxcr2^{-/-}$ mice develop severe APN and tissue damage after one week and relevance for human APN susceptibility has been demonstrated, through disease-associated IRF3 and CXCR1 polymorphisms in APN prone patients.

The cause of acute cystitis susceptibility has not been defined, however and it is rapidly becoming a therapeutic enigma as antibiotic resistance is reducing the options for treatment to a minimum. Genetic markers of APN susceptibility show no association to acute cystitis, emphasizing the differences in pathogenesis and genetic control. Acute uncomplicated cystitis is characterized by localized inflammation and symptoms from the lower urinary tract, typically dysuria and urgency and frequency of urination. It occurs predominantly in girls and healthy women with normal urinary tracts and at least 60% of all females will report an episode during their lifetime. The recurrence rate is high, especially in a subset of patients, where recurrent cystitis episodes may cause chronic tissue damage and impact the quality of life. In addition, acute cystitis patents pose a highly significant challenge to the health care system.

The urinary bladder mucosa is often under microbial attack but does not always retaliate with such force, as in acute cystitis. In asymptomatic carriers, the epithelium remains fairly unresponsive, despite bacterial numbers well above $10^5$ CFU/ml (9, 10). It is therefore challenging to understand, at the molecular level, how a state of exaggerated inflammation can be generated specifically in acute cystitis patients. Interactions of bladder cells with pathogenic bacteria have been shown to trigger an innate immune response, involving the epithelium and adjacent mucosal cells, such as mast cells and macrophages. Uroepithelial cells from women with recurrent cystitis have an increased density of receptors for adhering bacteria and bacterial persistence in intracellular communities has been studied as a reservoir of infection, but the molecular basis of susceptibility and disease has remained unclear.

SUMMARY OF THE INVENTION

The applicants have now identified for the first time, a cellular and genetic basis for acute cystitis susceptibility. In a screen for cytokines produced by infected human bladder cells, they discovered that about 85% of epidemiologically defined acute cystitis $E.\ coli$ strains triggered the secretion of IL-1β, a classical pro-inflammatory cytokine, which drives the pathogenesis of human inflammatory disorders. To address if the inflammasome controls host susceptibility to acute cystitis, bladder infection was established in mice lacking IL-1b, ASC (apoptosis-associated speck-like protein containing a CARD) or NLRP-3 (NACHT, LRR and PYD domains-containing protein 3) also known by cryopyrin). Consistent with such a role, mice were protected from pathology, as were $Casp1^{-/-}$ mice which have an IL-1β secretion deficiency. Remarkably, $Asc^{-/-}$ and $Nlrp3^{-/-}$ mice, which are deficient for inflammasome constituents, developed an IL-1β hyperactivation state with rapid, fulminant bladder inflammation and tissue damage, accompanied by massive neutrophil infiltration and upregulation of inflammasome genes. Mutations in these ASC or NLRP-3 genes in humans may therefore provide an indicator of susceptibility to disease, and also provide a prophylactic or therapeutic strategy for addressing disease.

The applicants have also identified a new mechanism of IL-1β processing which is responsible for this phenotype, involving the metalloproteinase MMP-7 in MMP-7 dependent processing and MMP-7 overexpression, in the bladder mucosa. The MMP-7 response may be explained by a direct effect of ASC and NLPR-3 on the MMP7 promoter, resulting in de-repression of Mmp7 expression in $Asc^{-/-}$ and $Nlrp3^{-/-}$ mice. As a consequence, the applicants found that treatment of $Asc^{-/-}$ mice by immunomodulation with the IL-1 receptor antagonist (IL-1RA) Anakinra or a metalloproteinase inhibitor prevented acute cystitis and pathology and $Il1b^{-/-}$ mice were protected. The results identify acute cystitis as a hyper-inflammatory condition caused by IL-1β hyperactivation and inflammasome dysregulation. It may be related to other IL-1β driven hyper-inflammatory disorders.

The present invention provides a method for treating cystitis comprising administering to a patient in need thereof, an effective amount of a reagent selected from the group consisting of IL-1β inhibitors and MMP inhibitors.

A method according to claim 1 wherein the cystitis is acute cystitis.

In particular, the reagent is an IL-1β inhibitor, and many such compounds are known in the art. These include for example, small molecules such as anthraquinones, described for example in U.S. Pat. No. 4,244,968 including diacerein, as well as proteins and peptides such as interleukin-1 receptor antagonist (IL-1 RA) for example anakinra, and rilonacept, or pharmaceutically acceptable salts thereof, or prodrugs thereof, and combinations of these. In particular, the reagent is an IL-1β receptor antagonist, such as anakinra (U.S. Pat. No. 5,075,222).

Alternatively, the reagent is an MMP inhibitor, and in particular an MMP7 inhibitor. A wide range of MMP inhibitors are known as described for example Durrant et al. Chem. Biol. Drug Des 20111; 78; 191-198, the content of which is incorporated herein by reference. Particular examples include batimastat, periostat (doxycycline hyclate), marimastat, or salts or prodrugs thereof, but in particular batimastat.

The invention further provides a reagent selected from the group consisting of IL-1β inhibitors and MMP inhibitors for use in the treatment of cystitis, in particular acute cystitis. Particular reagents are as described above.

The applicants have found that in patients suffering from cystitis have elevated levels of IL-1β and MMP-7 in urine, and thus these molecules act as diagnostic biomarkers. Hence, the invention further provides a method for diagnosing cystitis and in particular, acute cystitis, said method comprising detecting elevated levels of IL-1β or MMP-7 in urine of a subject. Suitable detection methods are known in the art, and include ELISA.

In yet a further aspect, the invention provides a method for diagnosing susceptibility to cystitis, said method comprising detecting a mutation in a gene encoding a protein selected from ASC or NLRP-3 which results in downregulation of said gene and/or in the expression of inactive protein. As the applicants have demonstrated, absence of these proteins leads to increased susceptibility to cystitis. Without being bound by theory, this may be due to the suppression of MMP-7 expression by these proteins, as discussed further below. Therefore, patients having a mutation which impacts on the expression of these proteins or the expression of functional proteins are likely to be at risk of developing cystitis as a result of elevation of MMP-7 levels.

Diagnosis may be carried out at the gene level, whereby the sequence of the Asc and/or Nlrp-3 is completely or partially determined and compared with a normal gene. For example, sites of common mutations that leads to inactivation or downregulation of the ASC or NLRP-3 proteins may be analyzed and the presence or absence of the selected mutation may be used to assess the likelihood that the patient is susceptible to cystitis.

Alternatively, diagnosis may be carried out at the protein level, where a suitable sample from a subject, such as a blood, serum, plasma or urine sample is analyzed for the presence of active ASC or NLRP-3 protein. Suitable methods in this case may include immunochemical assays such as ELISAs which use antibodies specific for the target proteins.

Once diagnosed, administration to the subject of the proteins or functional equivalents thereof, would be expected to prevent or treat disease. Thus in yet a further aspect, the invention provides a method for preventing or treating cystitis in a patient susceptible thereto as a result of a mutation which impacts on the expression of functional ASC or NLRP-3, which method comprises administering to said patient a protein selected from ASC or NLRP-3 or a functional fragment or variant thereof.

As used herein, the expression 'fragment' refers to a peptide or protein which lacks one or more amino acids found in a full length protein but which still has the function of the full length protein.

As used herein, the expression 'variant' refers to a peptide sequence in which the amino acid sequence differs from the basic protein or peptide sequence in that one or more amino acids within the sequence are substituted for other amino acids. However, the variant produces a biological effect which is similar to that of the basic sequence.

Amino acid substitutions may be regarded as "conservative" where an amino acid is replaced with a different amino acid in the same class with broadly similar properties. Non-conservative substitutions are where amino acids are replaced with amino acids of a different type or class.

Amino acid classes are defined as follows:

| Class | Amino acid examples |
| --- | --- |
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions may also be possible provided that these do not interrupt the function of the protein or peptide.

Broadly speaking, fewer non-conservative substitutions will be possible without altering the biological activity of the polypeptides.

In general, variants will have amino acid sequences that will be at least 70%, for instance at least 71%, 75%, 79%, 81%, 84%, 87%, 90%, 93% or 96% identical to the basic sequence. Identity in this context may be determined using the BLASTP computer program with the basic native protein sequence as the base sequence. The BLAST software is publicly available at http://blast.ncbi.nlm.nih.gov/Blast.cgi (accessible on 12 Mar. 2009).

Variants may also include addition sequences such as tag sequences that may be used for instance in facilitating purification of the peptide or in detection of it. Thus for instance, the variant may further comprise an affinity tag such as chitin binding protein (CBP), maltose binding protein (MBP), glutathione-S-transferase (GST), FLAG, myc, biotin or a poly(His) tag as are known in the art. In another embodiment, the variant may comprise a fluorescent protein such as green fluorescent protein (GFP).

In a further aspect, the invention provides a protein selected from ASC or NLRP-3 or a functional fragment or variant thereof, for use in the treatment of patients suffering from or susceptible to cystitis as a result of a mutation which impacts on the expression of functional ASC or NLRP-3 respectively.

For administration to patients, the reagent or protein is suitably administered in the form of a pharmaceutical composition, which further comprise a pharmaceutically acceptable carrier. Such compositions are known in the art.

Suitable pharmaceutical compositions will be in either solid or liquid form. They may be adapted for administration by any convenient route, such as parenteral, oral or topical administration or for administration by inhalation or insufflation. The pharmaceutical acceptable carrier may include diluents or excipients which are physiologically tolerable and compatible with the active ingredient.

Parenteral compositions are prepared for injection, for example either subcutaneously or intravenously. They may be liquid solutions or suspensions, or they may be in the form of a solid that is suitable for solution in, or suspension in, liquid prior to injection. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

Oral formulations will be in the form of solids or liquids, and may be solutions, syrups, suspensions, tablets, pills, capsules, sustained-release formulations, or powders. Oral formulations include such normally employed excipients as, for example, pharmaceutical grades of mannitol, lactose, starch, magnesium stearate, sodium saccharin, cellulose, magnesium carbonate, and the like.

Topical formulations will generally take the form of suppositories or intranasal aerosols. For suppositories, traditional binders and excipients may include, for example, polyalkylene glycols or triglycerides; such suppositories may be formed from mixtures containing the active ingredient.

The amount of reagent administered will vary depending upon factors such as the nature of the reagent being used, the size and health of the patient, the nature of the condition being treated etc. in accordance with normal clinical practice. Typically, a dosage in the range of from 1 μg-50 mg/Kg for instance from 2-20 mg/Kg, such as from 5-15 mg/Kg would be expected to produce a suitable effect.

The urinary bladder mucosa is often under microbial attack but rarely retaliates with full force. In asymptomatic carriers, the epithelium remains refractory despite bacterial numbers well above $10^5$ CFU/ml. Yet bacteria that cause acute cystitis create a state of exaggerated inflammation and the patients develop the characteristic symptoms of dysuria, frequency and pain. In this study, we elucidate molecular and cellular mechanisms underlying the exaggerated response that leads to acute symptoms and bladder pathology. We identify IL-1b as a crucial host sensor of bladder infection and inflammasome dysregulation as a cause of bladder pathology. In addition, the metalloproteinase MMP-7 is introduced as a new molecular player in mucosal inflammation, proteolytically cleaving IL-1b. The importance of IL-1b and MMP-7 is proven by treatment of susceptible mice with IL-1RA or MMP inhibitor. Elevated IL-1b levels were also detected in patients with acute cystitis compared to patients with ABU. This molecular basis of acute cystitis also provides as a new therapeutic approach using IL-1b and MMP-7 inhibitors as immune-modulators of acute cystitis.

IL-1b is a potent pro-inflammatory cytokine that initiates and amplifies innate immune responses. IL-1b production increases in response to viral, bacterial, fungal and parasitic infections and IL-1b is essential for the defense against microbial attack. IL-1b responses may also be detrimental, however, and dysregulation of IL-1b has been observed in autoimmune and auto-inflammatory disorders, such as rheumatoid arthritis, multiple sclerosis, Crohn's disease or neuro-degenerative disorders. This dichotomy was apparent also in the present study, where a controlled IL-1b response accompanied the clearance of infection in WT mice. The association of a dysregulated IL-1b response with disease suggested that acute cystitis is an infection-induced, hyper-inflammatory disorder of the urinary bladder. This is in contrast to *Salmonella* and *Shigella*, where Il1b$^{-/-}$ mice showed increased mortality rather than protection. The dramatic phenotype in Asc$^{-/-}$ and Nlrp3$^{-/-}$ mice raises the question if ASC and NLRP-3 dysfunctions may precipitate other hyper-inflammatory conditions, where pathology is associated with IL-1b and inflammasome responses.

The NLRP-3 inflammasome is activated by a number of microbial stimuli including LPS, MDP, bacterial RNA, poly(I:C) as well as ATP and bacterial pore-forming toxins. NLRP-3 activation stimulates the binding of ASC through homotypic pyrin domains and the caspase recruitment domain of ASC serves as an adaptor that binds NLRP-3 to pro-Caspase-1 to form the inflammasome. The dramatic disease phenotype in Asc$^{-/-}$ and Nlrp3$^{-/-}$ mice strongly suggested that a functional inflammasome response is required to maintain tissue homeostasis in infected bladders. Cystitis strains that were active IL-1b inducers also increased the expression of NLRP-3, ASC and Caspase-1 in human bladder cells and processing of IL-1b was detected, with secretion of the mature form into urine and cell supernatants. Furthermore, the presence of large quantities of IL-1b in the urine of Asc$^{-/-}$ and Nlrp3$^{-/-}$ mice demonstrated that pro-IL-1b is processed in these mice. Yet, effects of caspase inhibition were limited, suggesting that additional mechanisms must be involved.

Proteolytic cleavage by MMP-7 was identified as a new mechanism of IL-1b processing and evidence for IL-1b fragmentation by MMP-7 was obtained by direct cleavage of the purified components, in vitro. MMP-7 has metalloendopeptidase activity and is known to degrade collagen, proteoglycans, fibronectin, elastin and casein. MMP7 is activated following TNF-a or IL-1b stimulation of cells. It is commonly expressed in epithelial cells and has been shown to regulate the activity of defensins in the intestinal mucosa. By transcriptomic analysis, Mmp7 was identified as the most strongly activated gene in pathological bladders and the protein was mainly expressed in the bladder epithelium. The dramatic shedding of epithelial cells positive for IL-1β and MMP-7 may, thus, explain the elevated urine IL-1b levels in mice that developed pathology and the low IL-1b levels in mice treated with the MMP inhibitor. In the absence of inhibitor, this process resulted in a denuded mucosal surface, lacking a protective epithelial barrier. These morphological changes make it possible to understand the intense pain and symptoms in acute cystitis patients.

The results also emphasize the difference in pathogenesis between acute cystitis and acute pyelonephritis. The pathology in Asc$^{-/-}$ and Nlrp3$^{-/-}$ mice was bladder specific as there was no evidence of exaggerated inflammation in the kidneys. Conversely, Irf3$^{-/-}$ mice, which develop massive kidney pathology in response to CFT073 infection, showed no bladder pathology. This discrepancy emphasizes that bladder pathology is generated by mechanisms that differ from the well-known molecular interactions and signaling pathways that control acute pyelonephritis. Interestingly, this includes a difference in TLR4 dependence. Kidney pathology is controlled, to a large extent by TLR4 (7, 8), acting upstream of the IRF-3 and AP-1 transcription factors. Kidneys of Tlr4$^{-/-}$ mice therefore fail to respond to most UPEC strains and develop ABU. In contrast, a residual response was present in the bladders of Tlr4$^{-/-}$ mice, through MyD88 and NF-kB signaling, Il1b and Tnf expression, potentially suggesting a mechanism for the increased expression of IL-1b and IL-1b-dependent genes.

Recurrent acute cystitis is a handicap, socially, professionally and emotionally but despite its prevalence and importance for patients and society, acute cystitis is a poorly understood disease. Social and behavioral factors have been emphasized as a cause of recurrent infections and until recently, therapeutic options have included a variety of shorter or longer antibiotic regimens, many of which have been discontinued, due to resistance development. It comes as no surprise, that this highly painful condition has been the focus of various interventions in addition to antibiotic therapy. Deliberate establishment of competitive microflora has shown promising clinical effects, but novel, therapeutic approaches are needed in this large patient group. In this study, we show that acute cystitis is amenable to IL-1b receptor blockade in mice, given before infection and daily during the 7-day experiment. Inhibition of MMP-7 was also protective, but with a less complete phenotype than mice receiving the IL-1RA. As IL-1RA is in clinical use, testing immunotherapy with drugs like Anakinra as an adjunct to antibiotics may be a realistic option in acute cystitis patients.

FIGURE LEGENDS

The patent or application file contains at least one drawing executed in color. Copies of this patent or patent application publication with color drawing(s) will be provided by the Office upon request and payment of the necessary fee.

FIG. 1A-D. Acute cystitis strains activate IL-1β and inflammasome responses in human bladder epithelial cells.

Figure 1B:
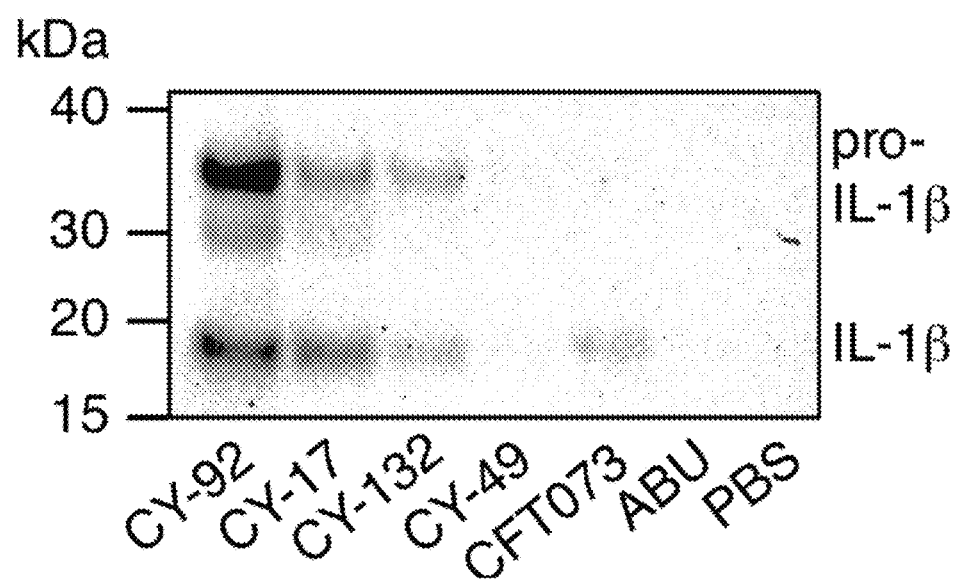
Figure 1C:
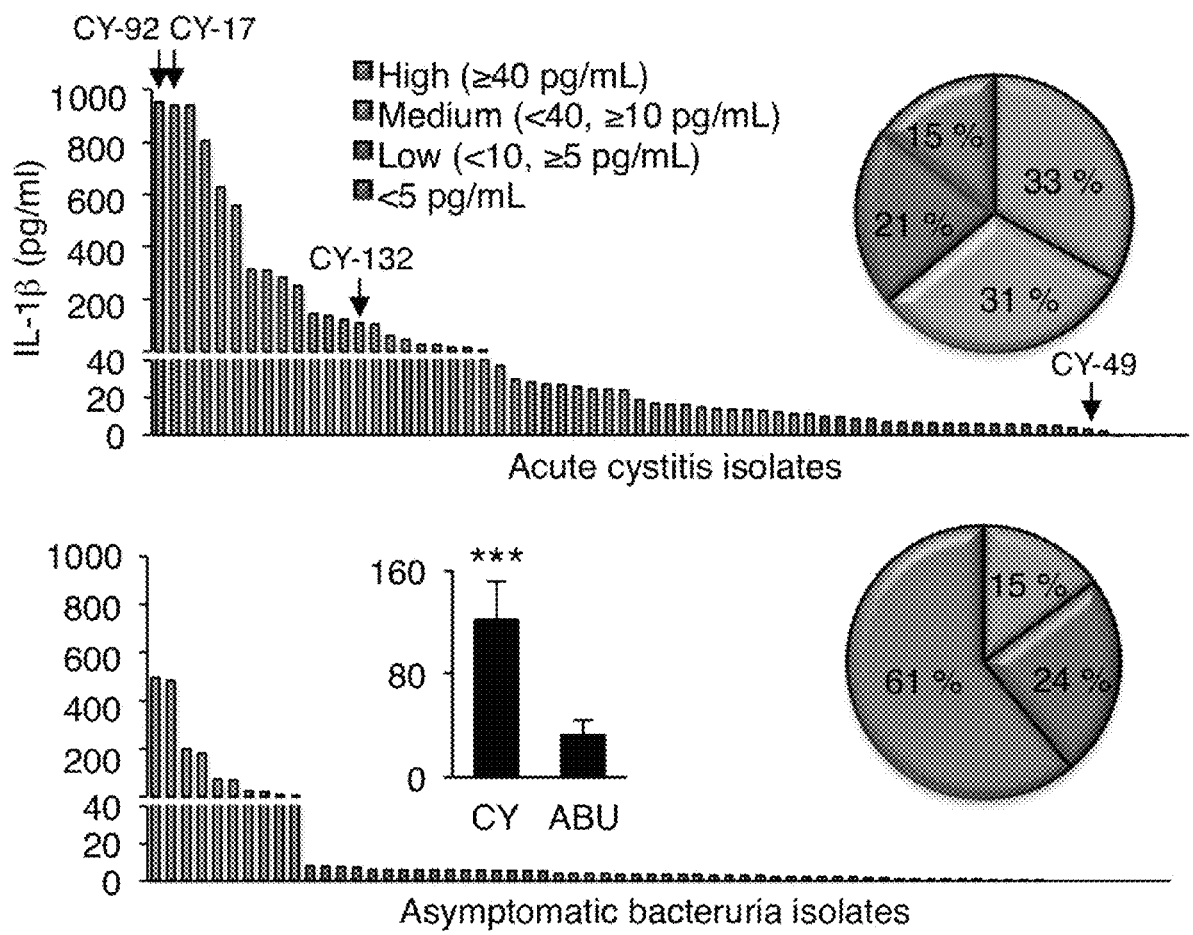
Figure 1D:
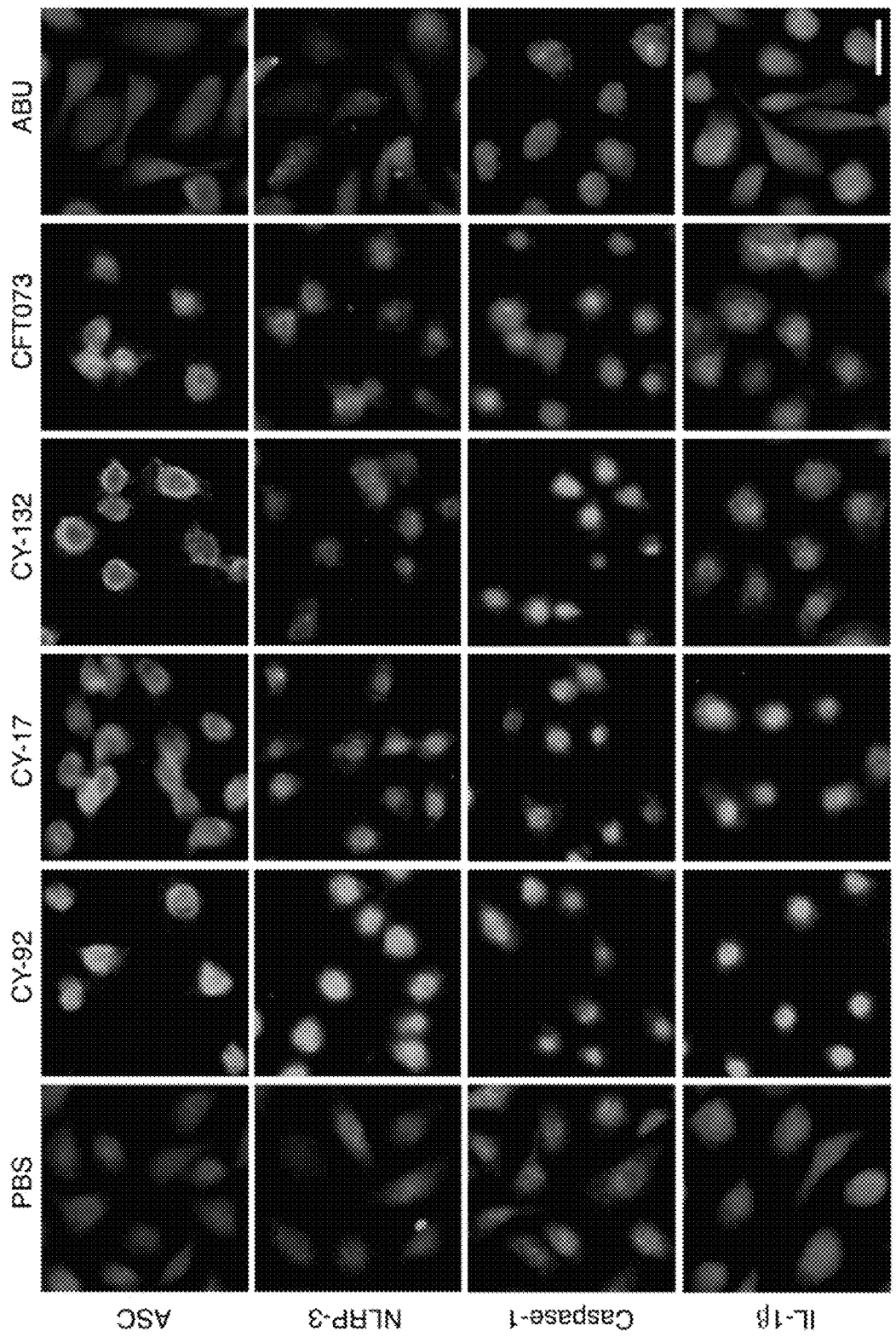

FIG. 1A IL-1β response in human bladder epithelial carcinoma cells (HTB-9) infected with acute cystitis strains CY-92, CY-17, CY-132 and CY-49 (108 CFU/ml, 4 hours). CFT073 and asymptomatic carrier strain E. coli 83972 (ABU) used as controls. IL-1β was quantified by ELISA, in cell supernatants (n=3, means±SEM, *P<0.05, two-tailed Mann Whitney test). FIG. 1B Increased pro-IL-1β and mature IL-1β levels in cells infected with CY-92, CY-17 and CY-132 (Western blot analysis of cell supernatants). FIG. 1C IL-1β response to an epidemiologically defined collection of paediatric acute cystitis strains (n=67) compared to ABU strains (n=66), obtained from children in the same geographic area. Pie chart indicating the frequency of bacterial strains activating IL-1β responses: high (orange), intermediate (blue), low (purple) or negative (green). Histogram (inset) of the mean IL-1β response to CY versus ABU strains (means±SEM, P<0.001, two-tailed Mann Whitney test). FIG. 1D Increased IL-1β and inflammasome protein staining (NLRP-3, ASC and Caspase-1) in human bladder cells infected with CY-17, CY-92, CY-132, CFT073 or ABU. Scale bar=20 µm.

FIG. 2A-D. Bladder pathology in infected Asc-/- and Nlrp3-/- mice.

Figure 2C:
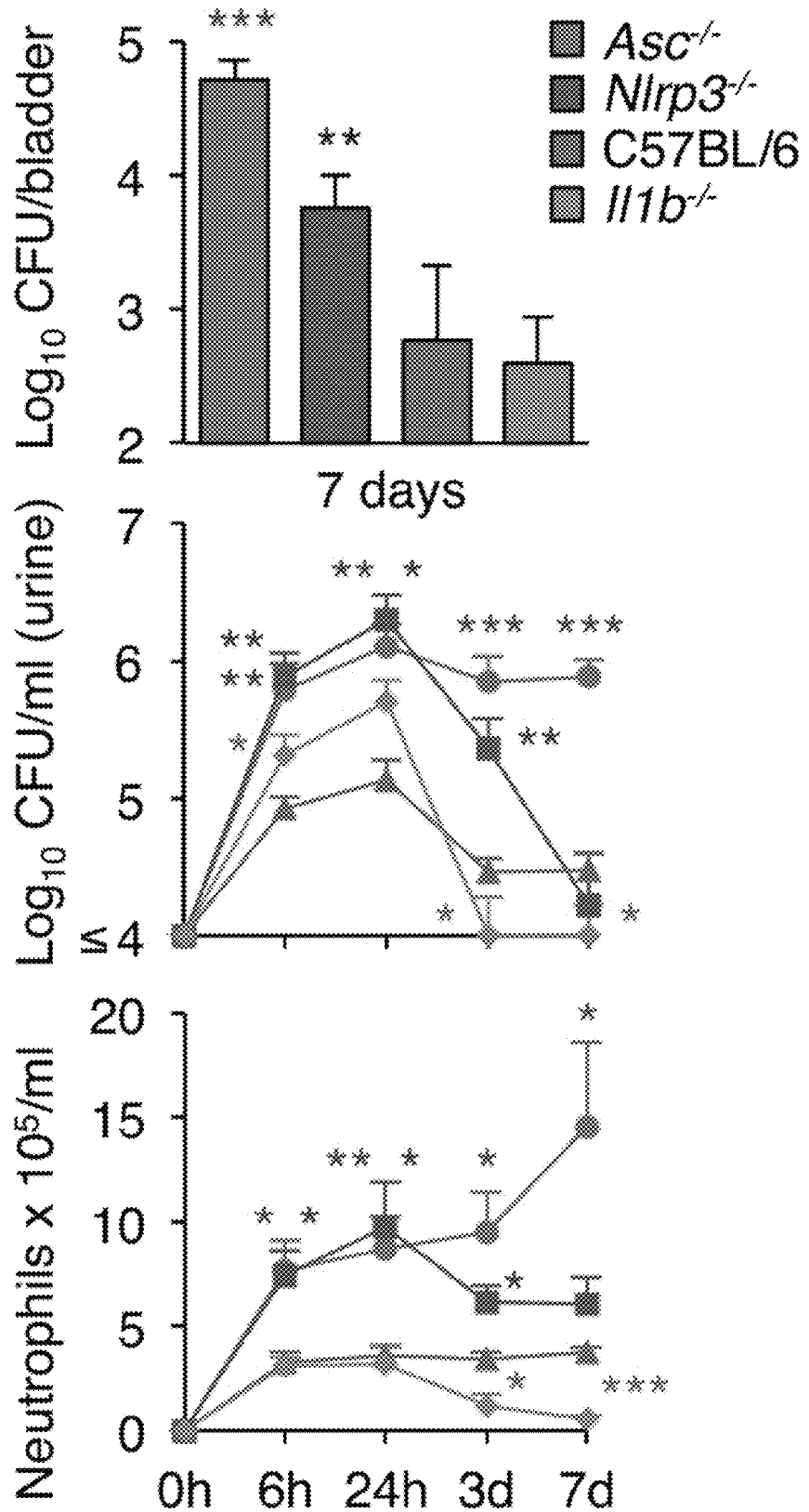
Figure 2D:
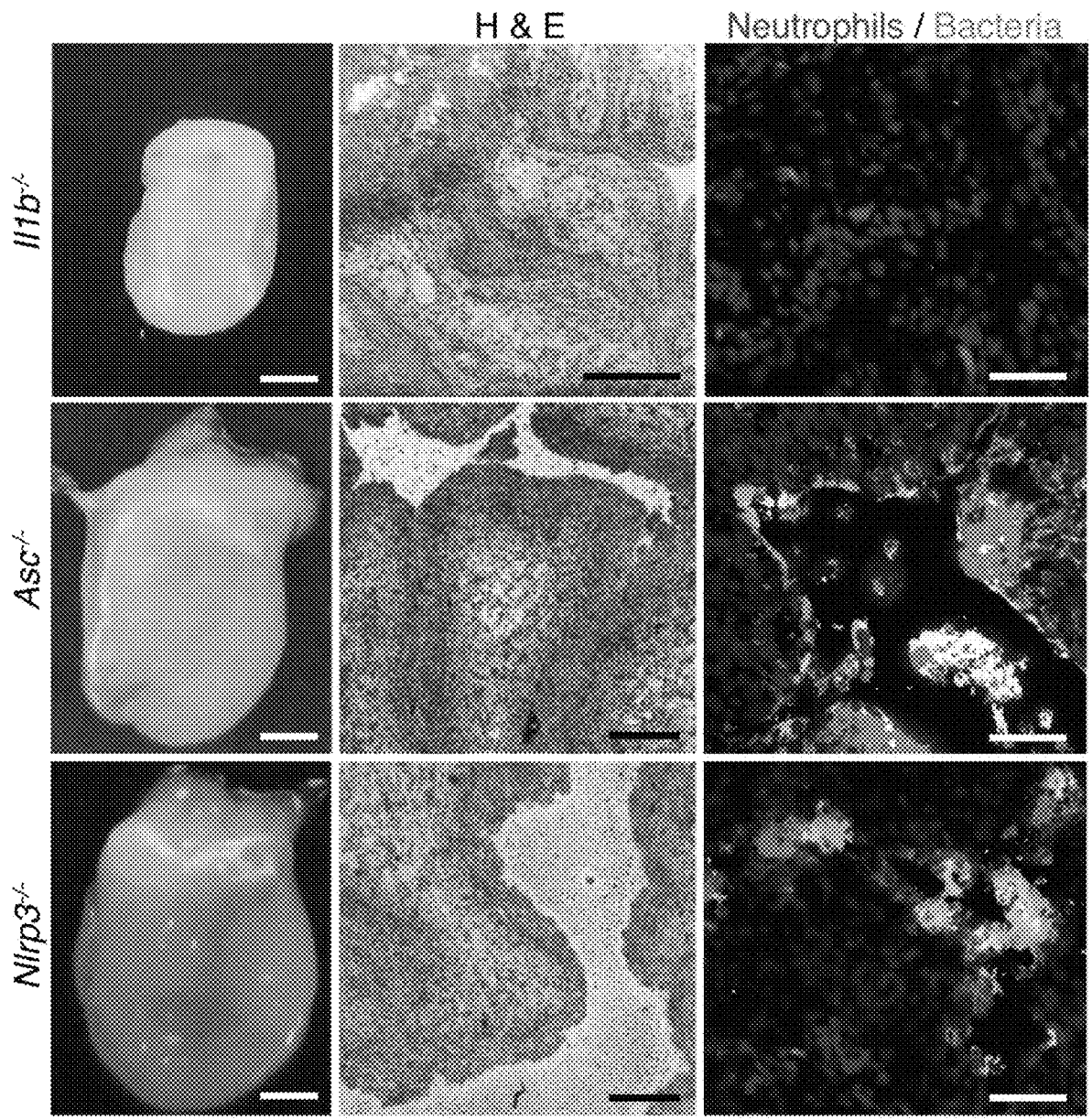

FIG. 2A Macroscopic bladder inflammation in WT mice infected with CY-17, CY-92 or CFT073 for seven days (left panels). Moderate edema and hyperaemia with a loss of structure in H&E-stained tissue sections (middle panels). Staining for bacteria and neutrophils, by immunohistochemistry (right panels). Scale bars=1 mm (whole bladders), 100 µm (H&E) and 50 µm (immunofluorescence). FIG. 2B Pathology scores (left panels). Kinetics of infection and neutrophil recruitment (n=4 per group, means±SEMs, P<0.01, *P<0.05, two-tailed unpaired t-test, compared to CFT073 infection). FIG. 2C Tissue response to infection in Asc-/- and Nlrp3-/- mice. Elevated bacterial counts in bladder and urine (upper panels) and neutrophil counts, compared to WT and Il1b-/- mice (n=10-14 per group, means±SEMs of two experiments, P<0.001, P<0.01, *P<0.05, two-tailed unpaired t-test compared to WT mice). FIG. 2D Macroscopic bladder pathology (left panels) in Asc-/- and Nlrp3-/- mice, 7 days after infection. Loss of structure in H&E-stained tissue sections (middle panels). Immunohistochemistry (right panels), showing bacterial/neutrophil infiltrates and micro abscesses along the mucosal border. Il1b-/- mice were protected against inflammation, with intact bladder morphology (H&E), few bacteria and low neutrophil counts (immunohistochemistry). Scale bars=1 mm (whole bladders), 200 µm (H&E) and 50 µm (immunofluorescence).

FIG. 3A-D. Hyper-activation of IL-1β dependent gene expression in Asc-/- and Nlrp3-/- mice.

Figure 3A:
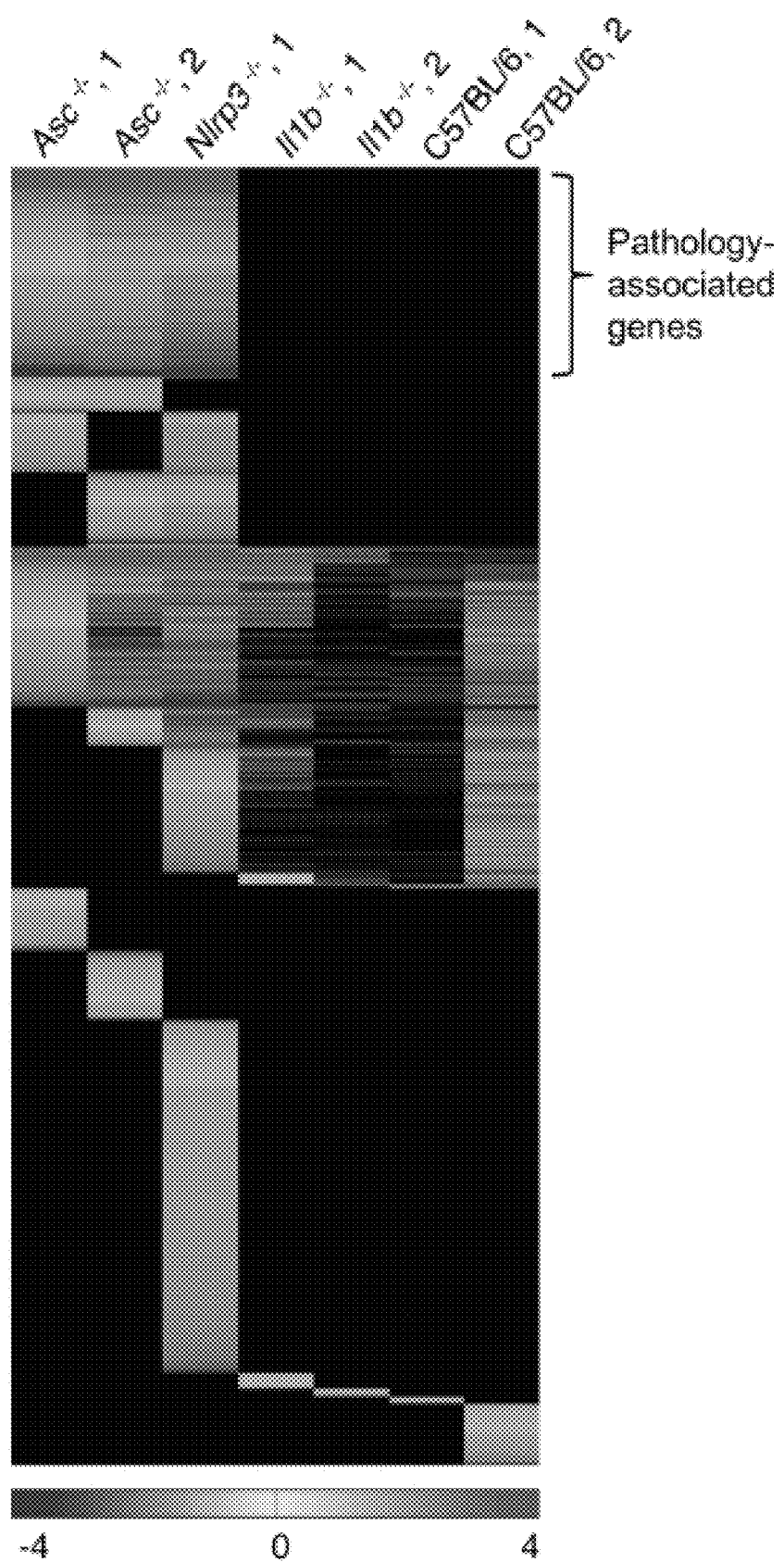
Figure 3B:
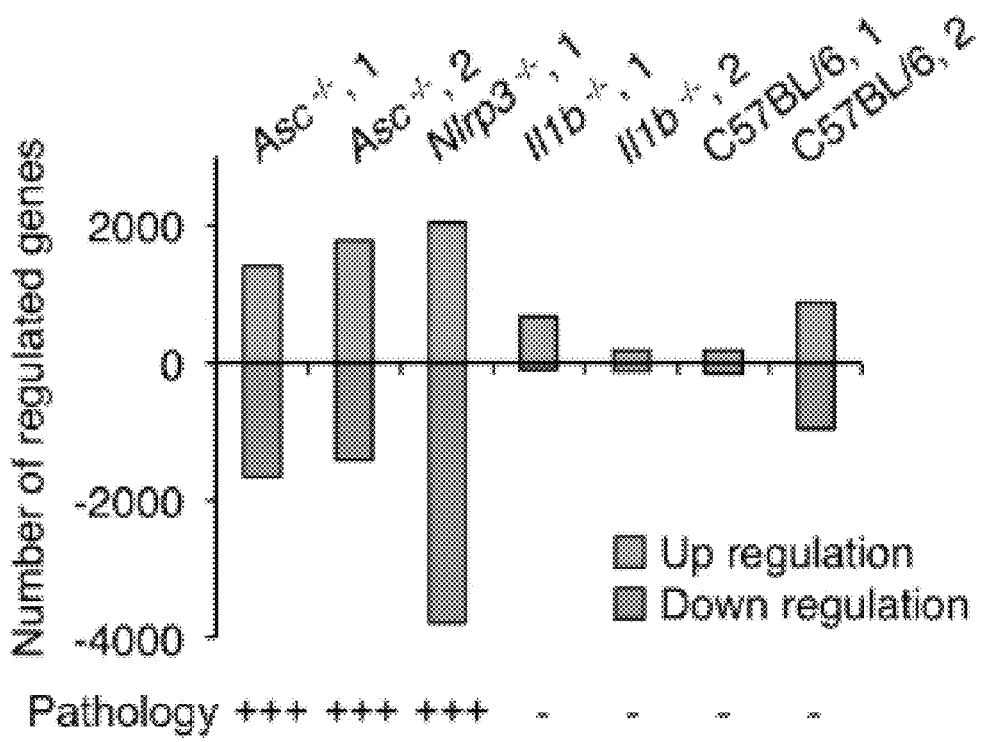
Figure 3C:
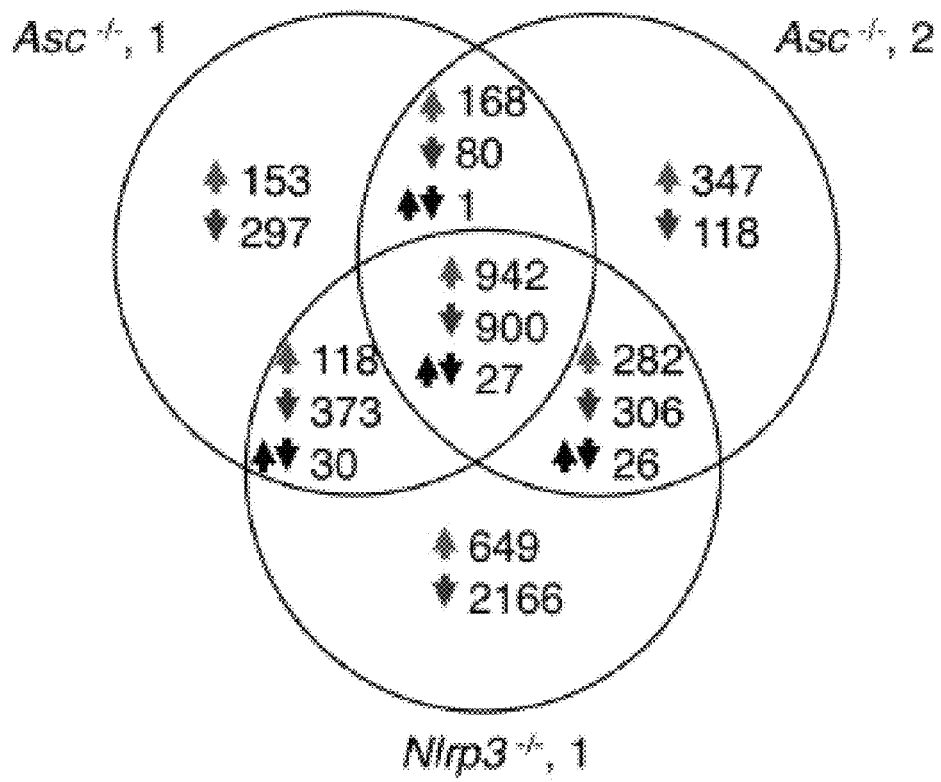
Figure 3D:
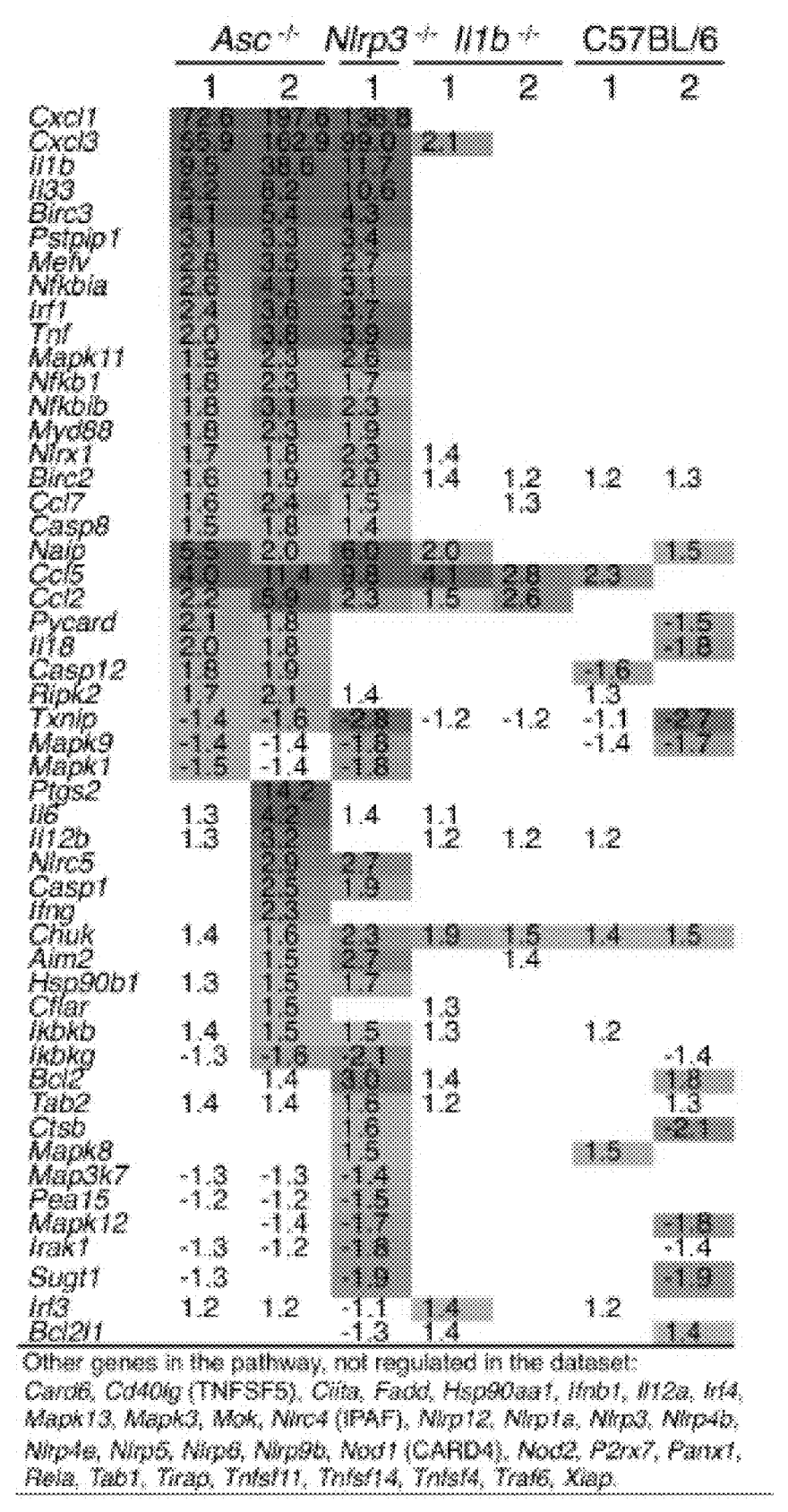

Reprogramming of host gene expression by infection, defined by transcriptomic analysis of whole bladder RNA from infected mice (7 days) compared to uninfected controls of each genotype (FC 1.41, P<0.05). FIG. 3A A distinct gene set distinguished the Asc-/- and Nlrp3-/- mice bladders with acute cystitis from mice without pathology (Heat map of differentially expressed genes). FIG. 3B Histogram quantifying the genotype-specific response to infection. From 3,000-6,000 genes were regulated in Asc-/- and Nlrp3-/- mice that developed acute cystitis compared to 300-2,000 genes in Il1b-/- and WT mice (P=0.014, unpaired t-test). FIG. 3C About 1800 genes regulated by infection in mouse bladders were shared among the mice that developed acute cystitis. FIG. 3D Massive over-expression of IL-1β and genes encoding inflammasome activators or downstream effectors in Asc-/- and Nlrp3-/- mice with acute cystitis but not in Il1b-/- and WT mice.

FIG. 4A-F. IL-1β processing by MMP-7.

Figure 4C:
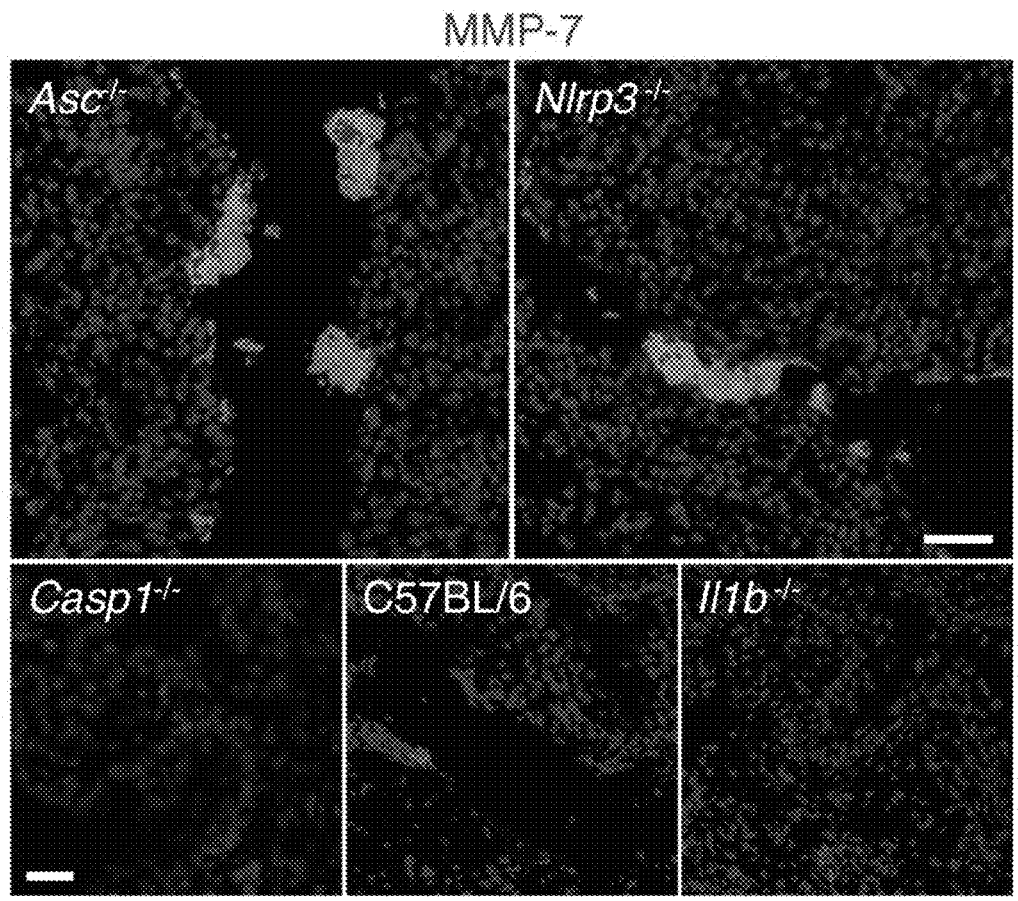
Figure 4D:
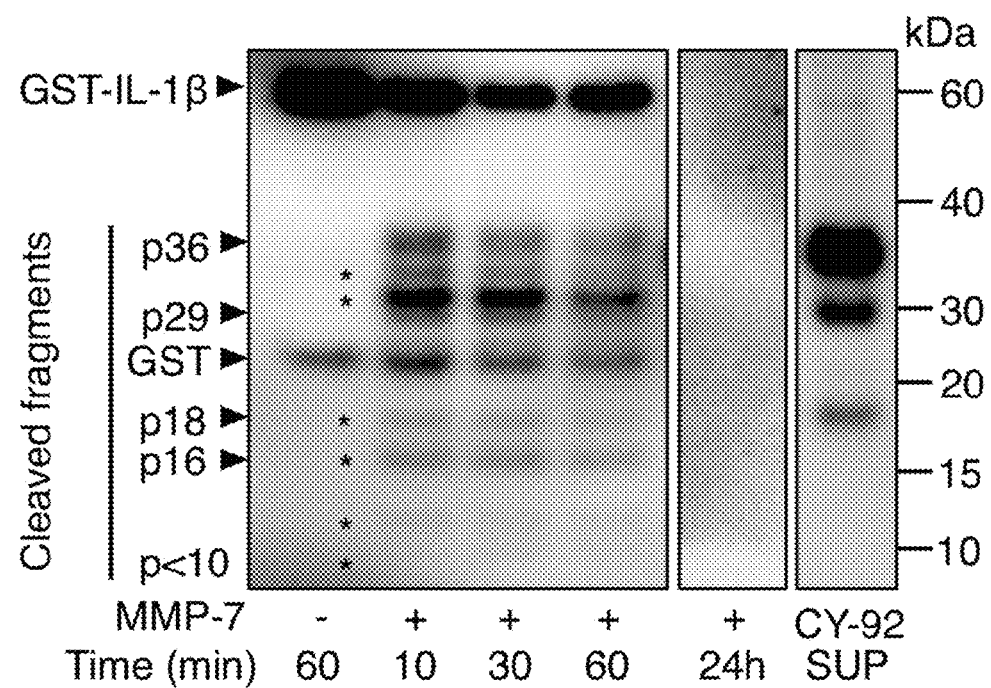
Figure 4E:
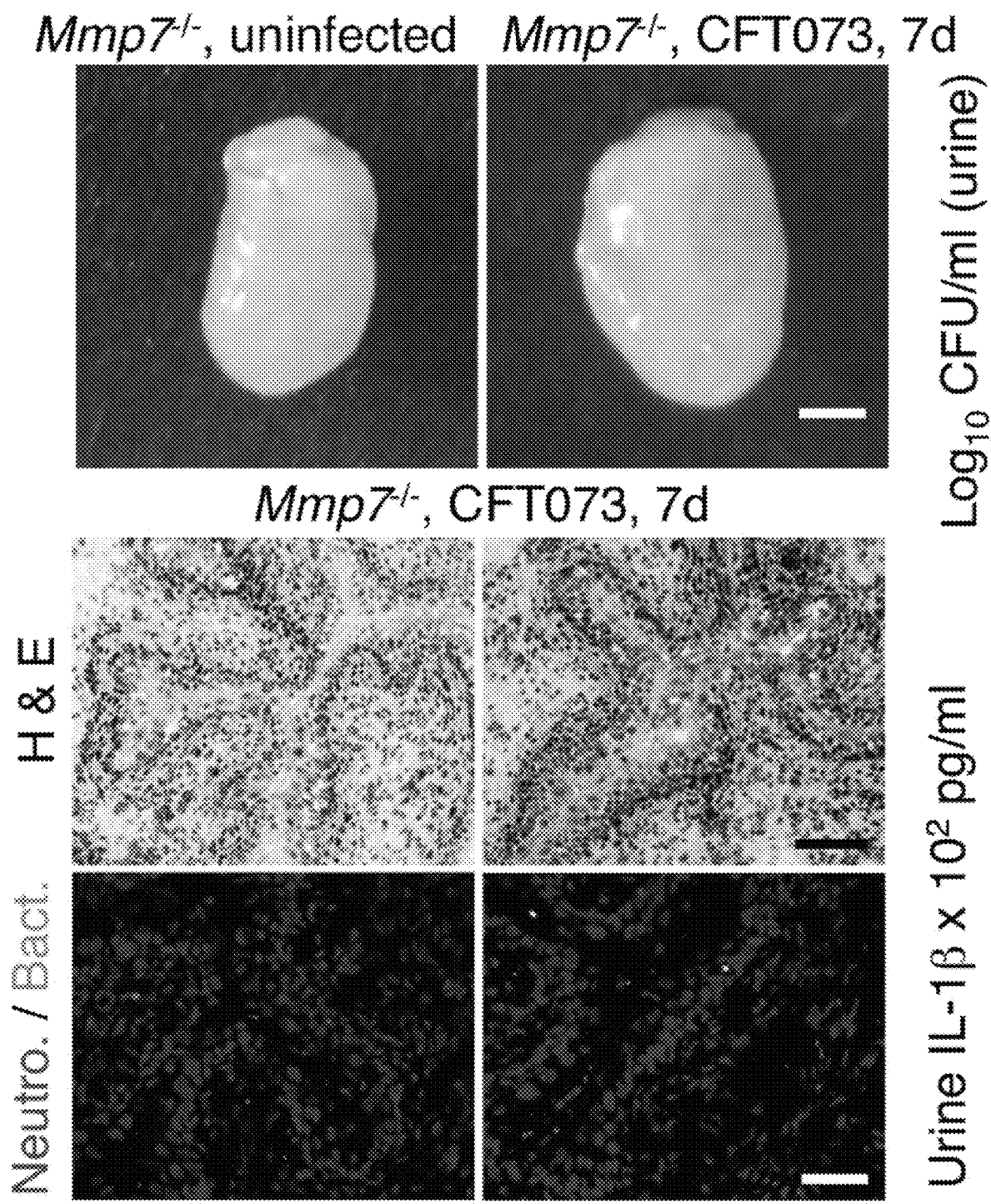
Figure 4F:
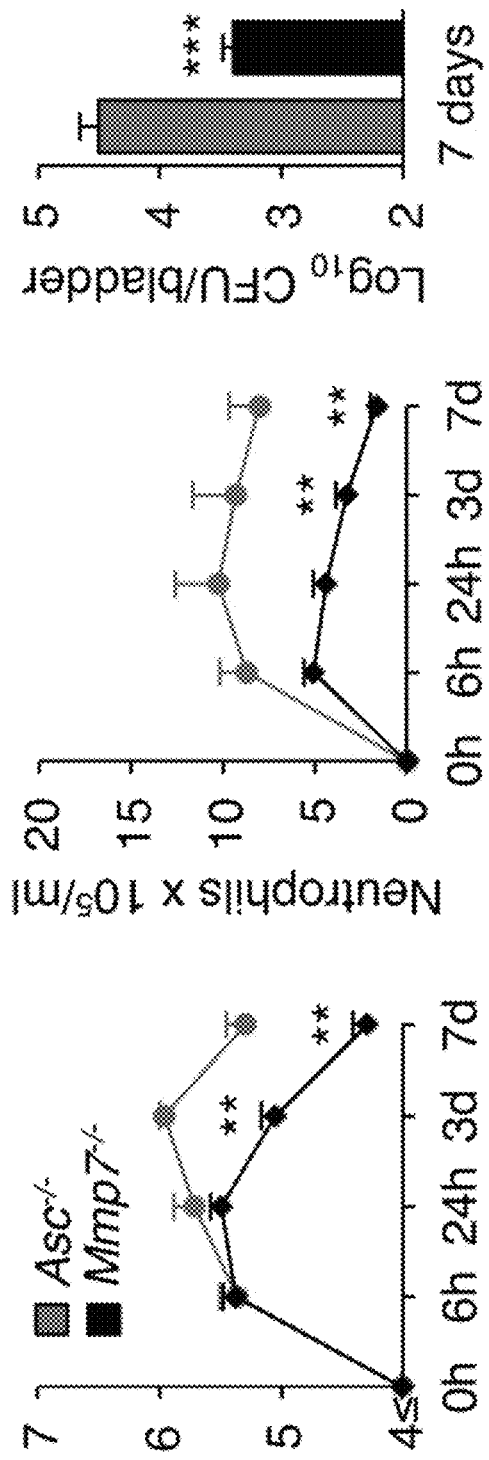
Figure 4F:
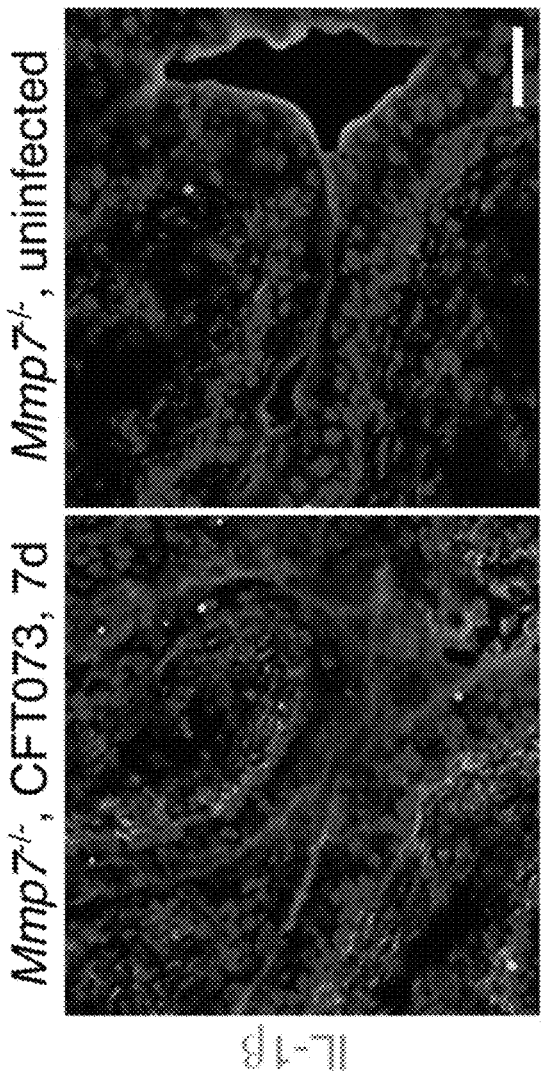
Figure 4F:
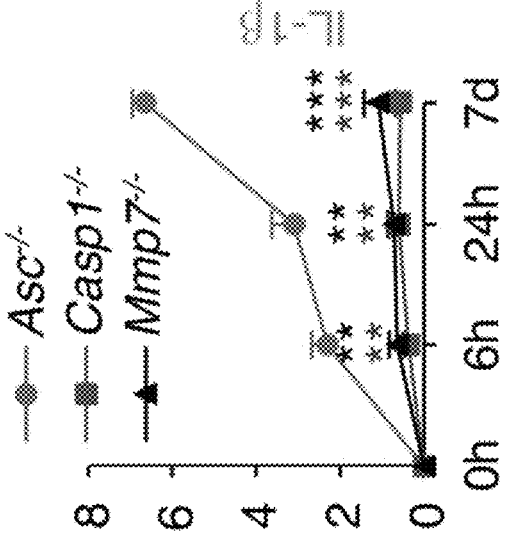

FIG. 4A Gene expression profiling of whole bladder mRNA identified Mmp7 as the top up-regulated gene in Asc-/- and Nlrp3-/- mice with bladder pathology (CFT073 infected mice, 7 days). FIG. 4B Mmp7 expression quantified by qRT-PCR (n=2 mice per group, mean±SEMs). FIG. 4C Epithelial MMP-7 staining in Asc-/- and Nlrp3-/- mice with bladder pathology. Scale bars=50 µm. FIG. 4D Proteolytic cleavage of Il-1β by MMP-7 in vitro, using purified enzyme and GST-tagged IL-1β. Arrows indicate cleavage products. The proteolytic IL-1β fragments were of similar size as the bands detected in supernatants of bladder cells infected with CY-92. FIG. 4E Lack of pathology in Mmp7-/- mice, 7 days after infection with CFT073. Low bacterial and neutrophil counts in urine compared to Asc-/- mice (n=5 per group, means±SEMs, P<0.01, two-tailed unpaired t-test). Scale bar=1 mm (whole bladders), 100 µm (H&E) and 50 µm (immunofluorescence). FIG. 4F Elevated IL-1β secretion into the urine of Asc-/- mice, but not Casp1-/- or Mmp7-/- mice. Limited retention of IL-1β in bladder tissue of Mmp7-/- mice, 7 days after infection. Scale bar=50 µm.

FIG. 5A-E. Regulation of MMP7 expression by ASC and NLRP-3.

Figure 5C:
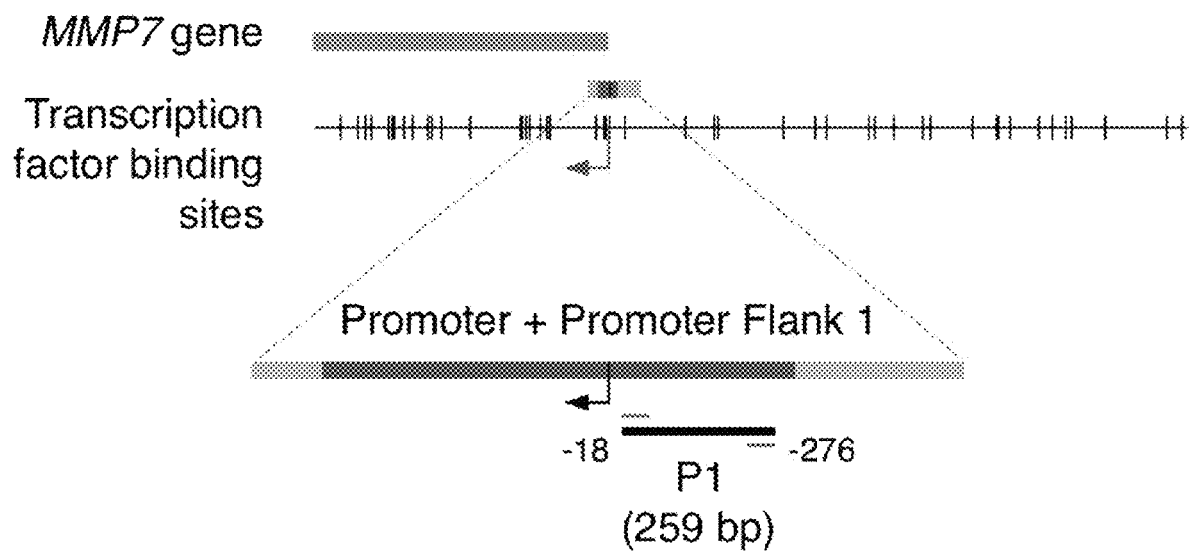
Figure 5D:
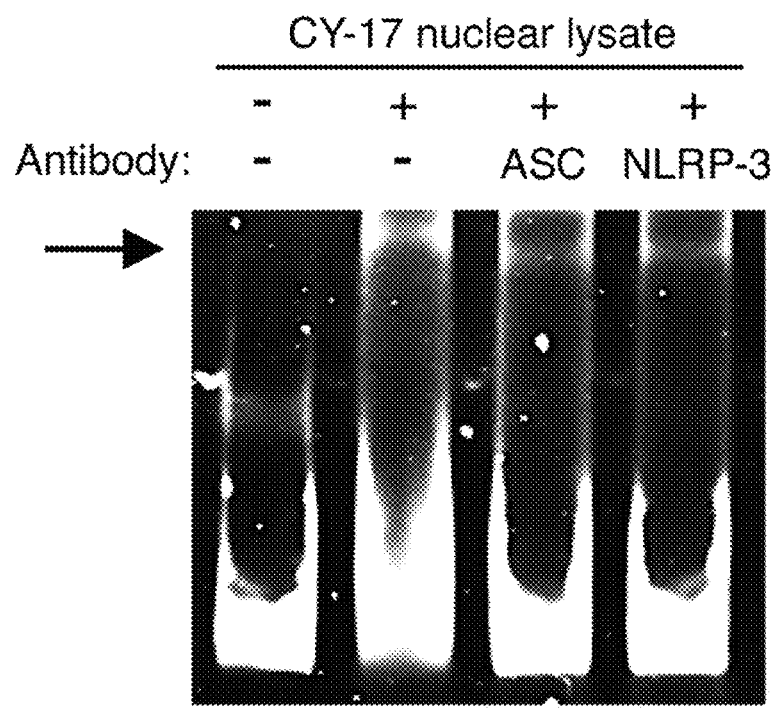
Figure 5E:
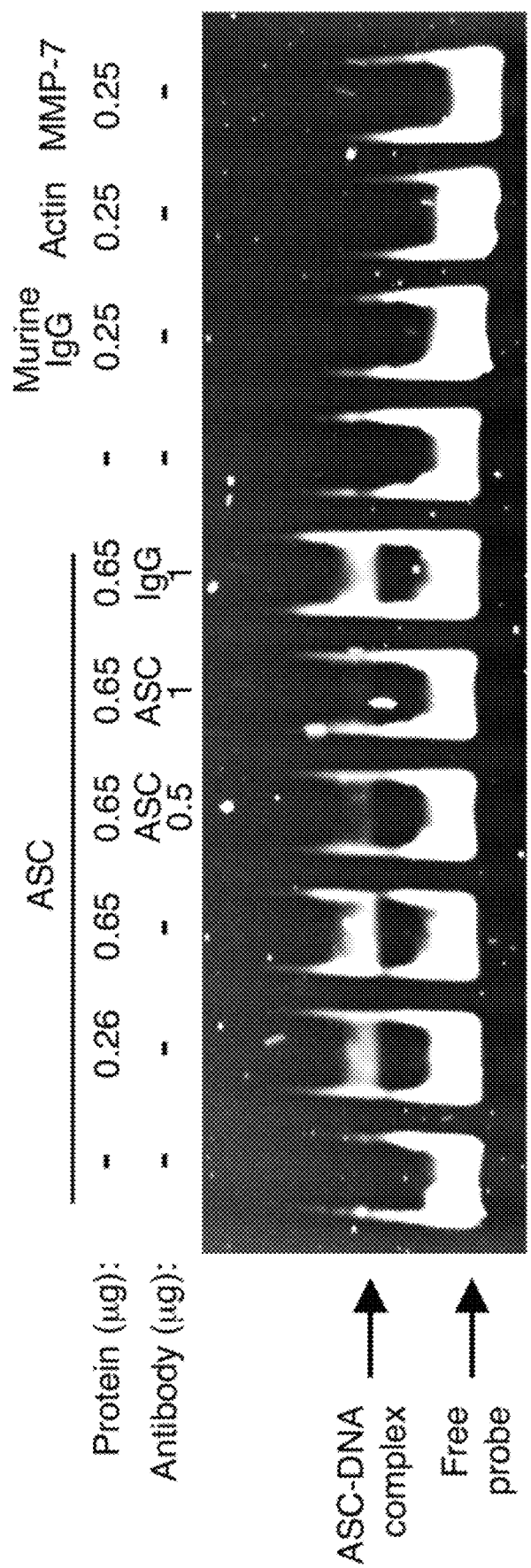

FIG. 5A MMP-7 response to infection with CY-17, visualized 739 by confocal microscopy. Massive increase in MMP-7 staining after transfection with ASC or NLRP3 specific siRNAs (left panels, scale bar=20 µm). FIG. 5B Western blot, confirming the knock-down of ASC or NLRP-3. FIG. 5C PCR amplification of a 259 bp fragment in the MMP7 promoter (P1, 743-18/-276 relative to transcription start site). FIG. 5D EMSA of a nuclear extract from CY-17 infected HTB-9 cells and P1. Binding identified as a band shift (arrow), was inhibited by ASC- or NLRP-3 specific antibodies. Free DNA forms a single low molecular weight band. FIG. 5E EMSA of the 259 bp MMP7 promoter fragment P1 and recombinant ASC. The dose-dependent formation of an ASC-P1 complex is shown as a band shift, which was inhibited by anti-ASC antibodies. IgG was used as negative control. Negative control proteins (murine IgG, bovine actin and MMP-7) did not cause a band shift.

FIG. 6A-E. Acute cystitis immunotherapy, using an IL-1 receptor antagonist (IL-1RA) or an MMP inhibitor.

Figure 6A:
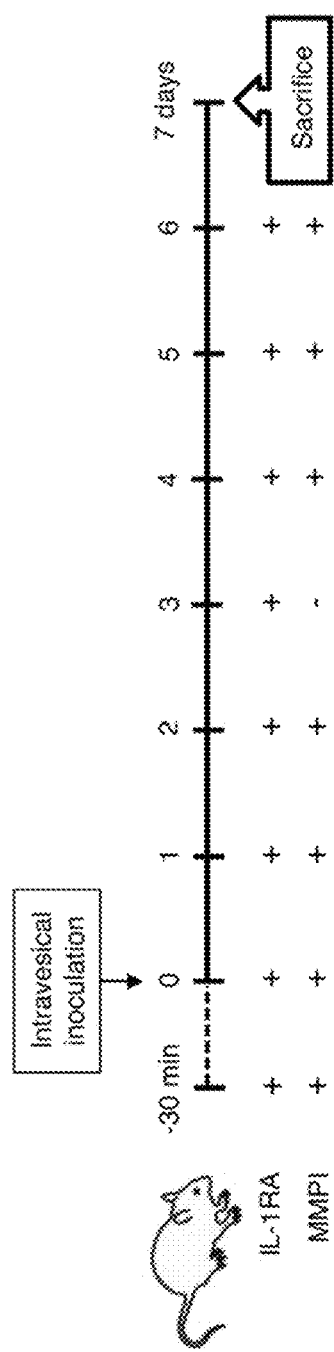
Figure 6B:
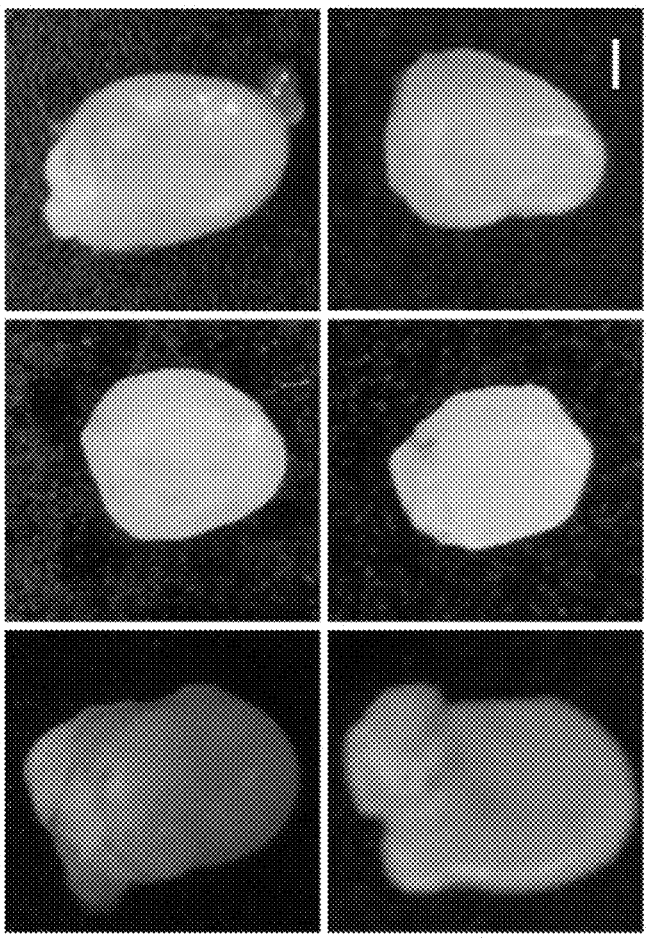
Figure 6C:
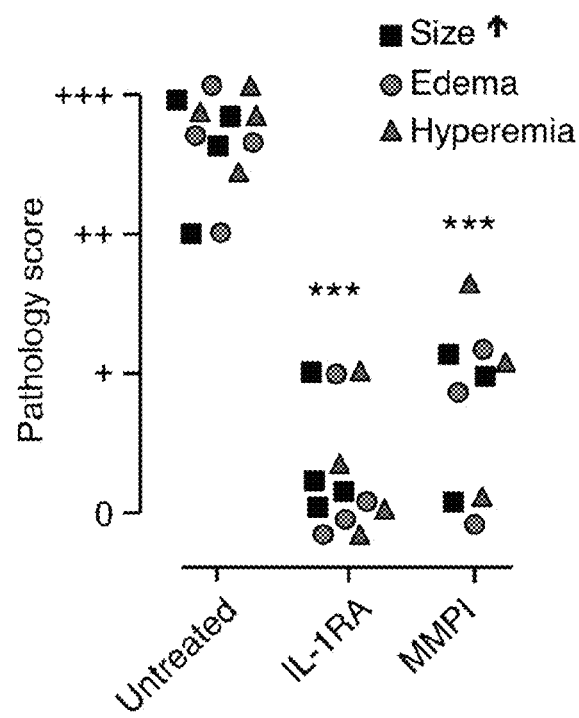
Figure 6D:
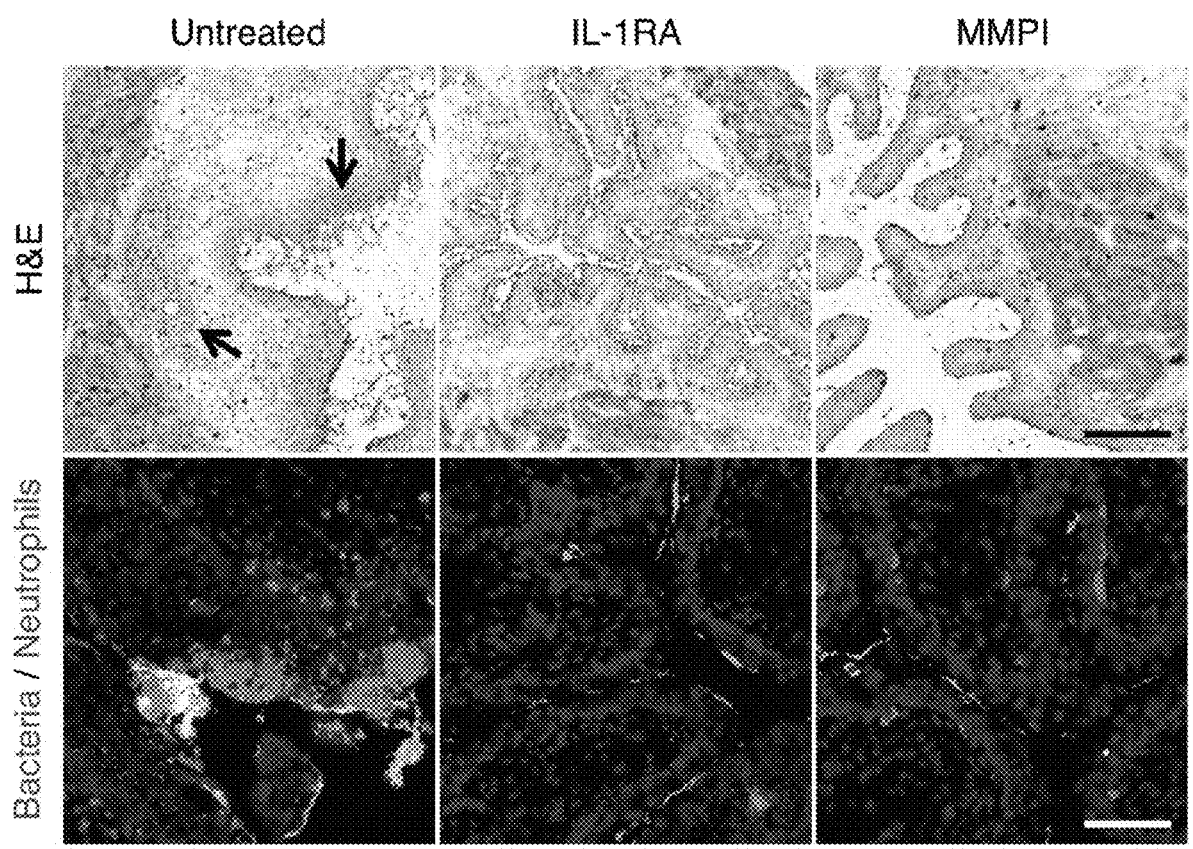
Figure 6E:
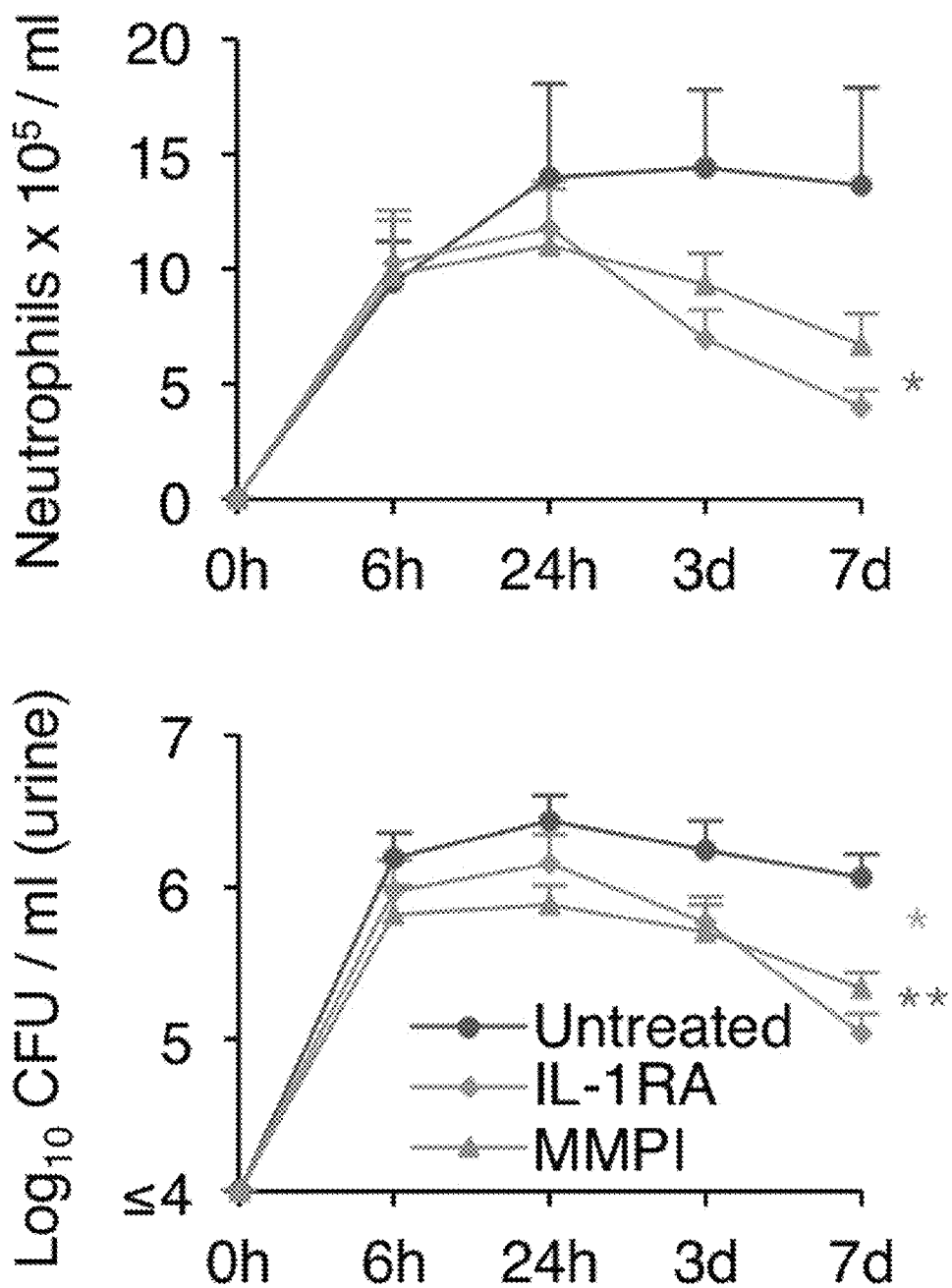

FIG. 6A Anakinra (IL-1RA) protects susceptible Asc-/- mice from acute cystitis. The mice were pre-treated with Anakinra, 30 min before infection and daily after infection with E. coli CFT073 (1 mg in 100 µl of PBS i.p. per mouse) Alternatively, Asc-/- mice were pre-treated with the matrix metalloproteinase inhibitor (MMP1) Batimastat, 30 minutes before infection and daily after infection with E. coli CFT073 (0.5 mg in 100 µl of PBS i.p. per mouse, except day 3). FIG. 6B IL-1RA prevented macroscopic bladder pathology in Asc$^{-/-}$ mice, as did the MMP1. Scale bar=1 mm. FIG. 6C The disease severity score was reduced by the inhibitors (n=3-4, ***P<0.001, compared to untreated Asc$^{-/-}$ mice, Fisher's exact test). FIG. 6D Protection from bladder tissue pathology in treated mice (H&E). Arrows indicate mucosal sloughing, edema and subepithelial abscesses in untreated mice. Loss of neutrophil aggregation in bladder sections from treated mice. Scale bar=200 μm (H&E) and 50 μm (immunofluorescent staining). FIG. 6E Neutrophils and bacteria in the urine of IL-1RA or MMPI treated Asc−/− mice, compared to untreated mice, 7 days after infection with CFT073 (n=3-4, means±SEM, P<0.01, *P<0.05, two-tailed unpaired t-test).

Figure 7A:
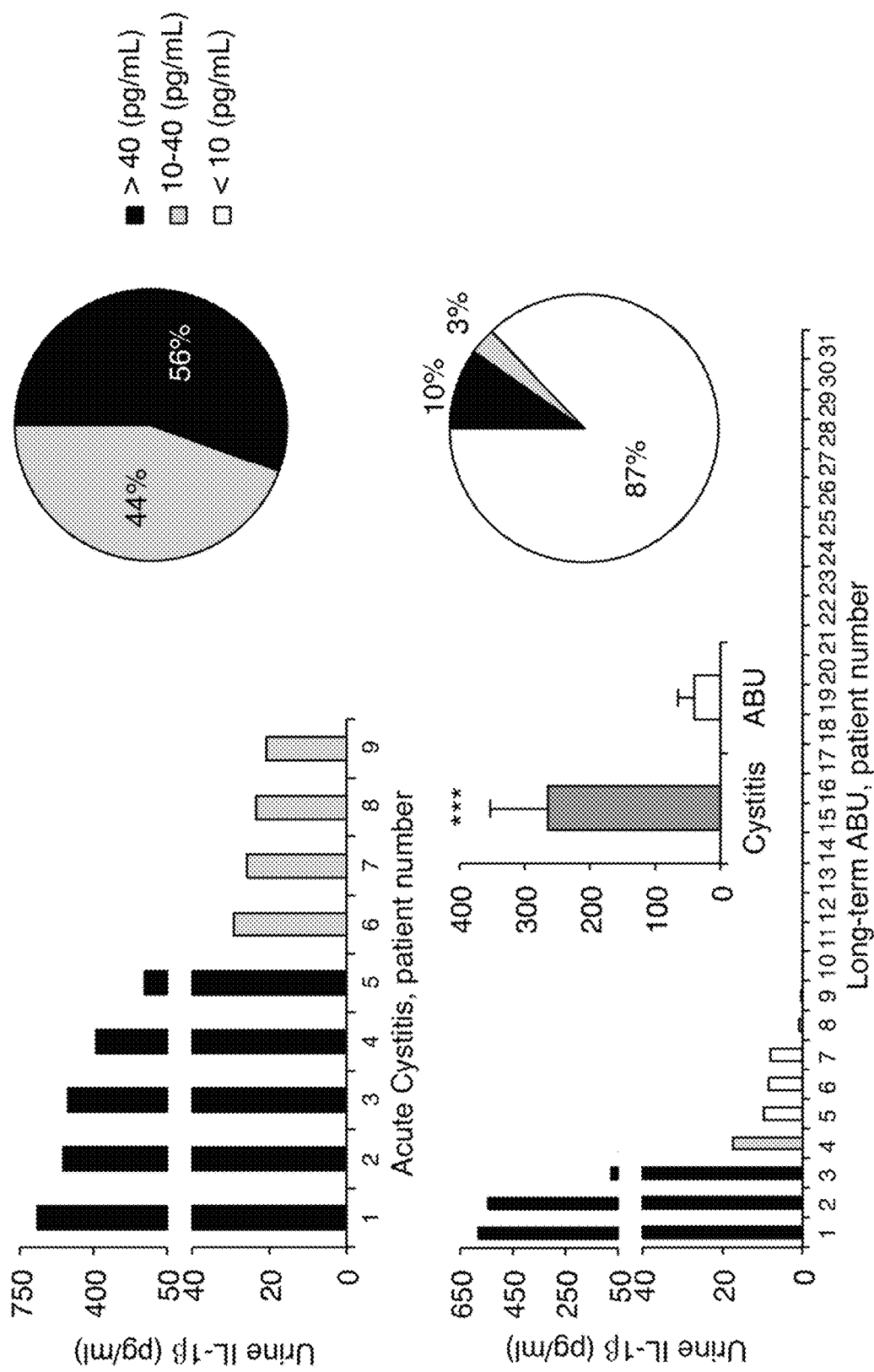
Figure 7B:
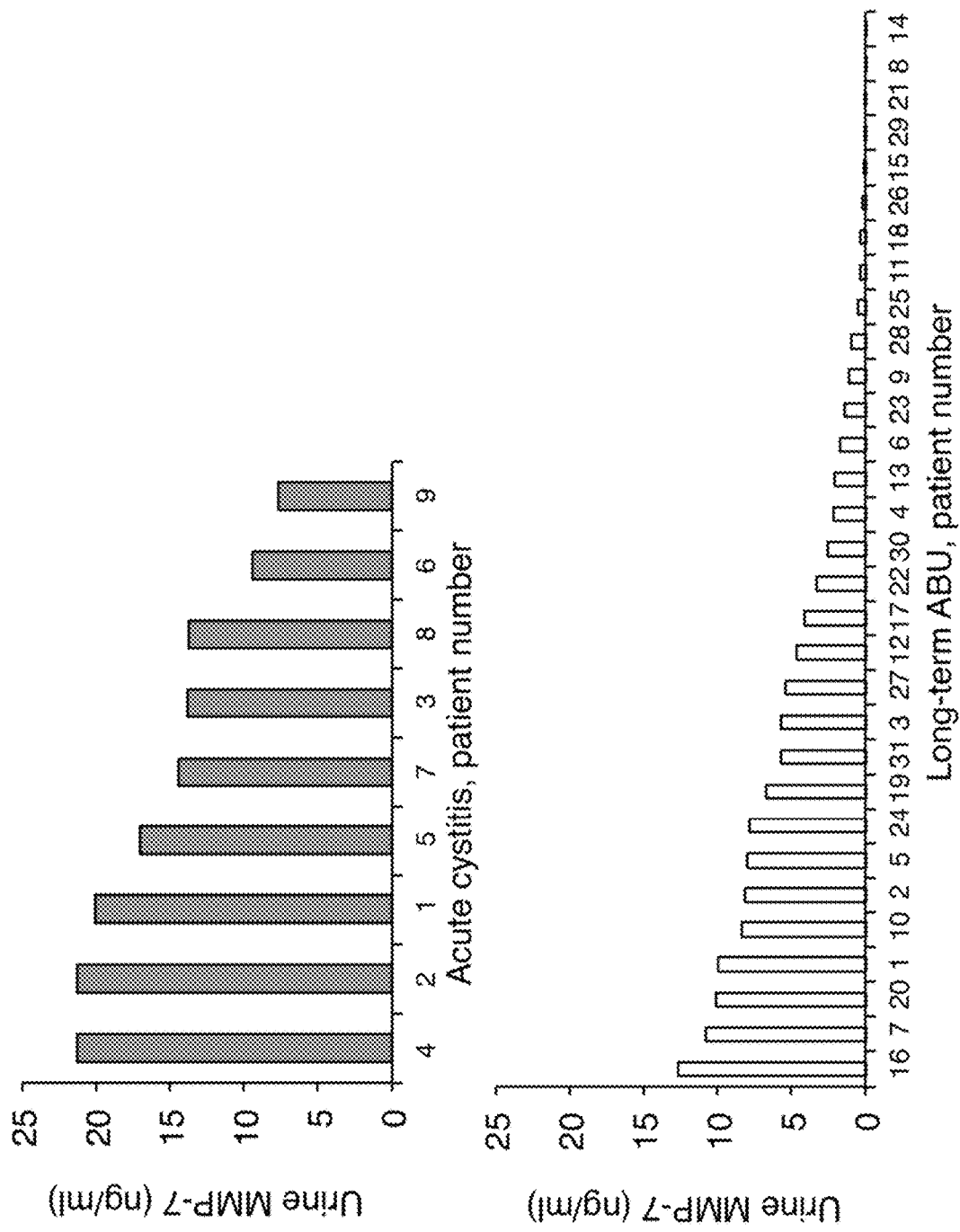

FIG. 7A-B. Elevated concentrations of IL-1β and MMP-7 in the urine of patients with acute cystitis.

FIG. 7A IL-1β concentrations were higher in urine samples from patients with acute cystitis (n=9) than in patients with ABU, who were asymptomatic carriers of E. coli 83972 (n=31). Histogram (inset) compares mean IL-1β concentrations between the two patient groups (mean±SEM, P<0.001, two-tailed Mann Whitney test). FIG. 7B MMP-7 concentrations were higher in urine samples from patients with acute cystitis than in patients with long-term ABU (***P<0.001, two-tailed Mann Whitney test). Urine samples were obtained at the time of diagnosis from patients with sporadic acute cystitis and from patients with ABU, who carried E. coli 83972 after therapeutic inoculation (9).

DETAILED DESCRIPTION OF THE INVENTION

Example 1

Methods and Materials

Patients with acute cystitis were enrolled at two primary care clinics. A diagnosis of acute cystitis was based on a urine dipstick analysis positive for bacteria and symptoms from the lower urinary tract, including frequency, dysuria and suprapubic pain. Midstream urine specimens were obtained at the time of diagnosis.

Patients with ABU were included in a placebo-controlled study of intravesical inoculation with E. coli 83972 (Sunden F, et al. The Journal of urology. 2010; 184(1):179-85). Briefly, E. coli 83972 bacteriuria was established by intravesical inoculation ($10^5$ CFU/ml in saline), daily for three days and the outcome was measured as the total number of UTIs during an optimal period of 12 months followed by a cross over to a similar period without E. coli 83972 bacteriuria. Urine samples were obtained for cytokine analysis during E. coli 83972 bacteriuria and symptom scores were registered. Urine IL-1β or MMP-7 levels were quantified by ELISA with Human Il-1b/IL-1F2 DuoSet ELISA kit and Human total MMP-7 Immunoassay Quantikine® ELISA respectively (both from R&D Systems).

Bacterial Strains

Cystitis (CY) and asymptomatic bacteriuria (ABU) strains were prospectively isolated during a study of childhood UTI in Göteborg, Sweden (Lindberg U, et al. The Journal of pediatrics. 1978; 92(2):194-9). The UPEC strain, E. coli CFT073 (06:K2:H1) (Nielubowicz G R, et al. Nature reviews Urology. 2010; 7(8):430-41), and ABU strain E. coli 83972 (OR:K5:H-) were controls. Bacteria were cultured on tryptic soy agar (TSA, 16 h, 37° C.), harvested in phosphate-buffered saline (PBS, pH 7.2) and diluted as appropriate. Overnight static cultures of E. coli CFT073 in Luria-Bertani (LB) broth were used for experimental infection.

Cell Culture

Human bladder (5637, ATCC #HTB-9) and kidney epithelial cells (A498, ATCC #HTB-44) were cultured to 70-80% confluence on 8-well chamber slides ($6\times10^4$ cells/well) or in 6-well plates ($6\times10^5$ cells/well) in RPMI-1640 (Thermo Scientific) supplemented with 1 mM sodium pyruvate, 1 mM non-essential amino acids, gentamicin (50 μg/ml) (GE Healthcare) and 10% heat-inactivated fetal bovine serum (PAA) at 37° C. with 5% $CO_2$.

Cytokine Measurements

IL-1β, IL-6 and IL-8 concentrations in filtered supernatants (Syringe Filter w/0.2 um PES, VWR) were determined by Immulite 1000 (Siemens) and Il-1β concentrations in cell supernatants or urine by Human or Mouse Il-1b/IL-1F2 DuoSet ELISA kits (R&D Systems). Urine MMP-7 levels were quantified with Human total MMP-7 Immunoassay Quantikine® ELISA (R&D Systems).

Confocal Microscopy

Cells were grown as described above, infected, fixed (3.7% formaldehyde, 10 min), permeabilized (0.25% Triton X-100, 5% FBS, 15 min), blocked (5% FBS, 1 hour at room temperature), incubated with primary antibodies in 5% FBS overnight at 4° C. (rabbit anti-IL-1 beta (ab9722), anti-TMS1 (ASC) (ab155970), anti-caspase-1 (ab62399, all Abcam) or mouse anti-CIAS1/NLRP3 (ab17267, Abcam) and appropriate fluorescently labeled secondary antibody (Alexa Fluor® 488 goat anti-rabbit IgG (#A-11034) and goat Anti-Mouse IgM (#A-11001, both Life Technologies), (1 hour at room temperature). After nuclear staining (DRAQ5, Abcam), slides were mounted (Fluoromount, Sigma-Aldrich), imaged by laser-scanning confocal microscopy (LSM510 META confocal microscope, Nikon Eclipse C1) and quantified by ImageJ software 1.46r (NIH).

Western Blotting

Cells were cultured as described above, but in particular in 6-well plates ($7\times10^5$ cells/well, Thermo Fisher Scientific), lysed with RIPA lysis buffer, supplemented with protease and phosphatase inhibitors (Roche Diagnostics). They may then be fractionated using NE-PER Nuclear and Cytoplasmic extraction reagents (Thermo Scientific). For Caspase inhibition, cells were pre-incubated with Z-VAD(OMe)-FMK (#BML-P416-0001, Enzo Life Science, 100 μM, 30 min). Supernatants were filtered and concentrated by trichloroacetic acid precipitation, followed by acetone desiccation. Lysates and supernatants were run on SDS-PAGE (4-12% Bis-Tris gels, Invitrogen), blotted onto PVDF membranes which were blocked with 5% bovine serum albumin (BSA) or non-fat dry milk (NFDM) and incubated with primary antibody: rabbit anti-IL-1 beta (1:2 000, or 1:2,500 in 5% NFDM, ab9722), rabbit anti-ASC (1:200 in 5% BSA, sc-22514-R, Santa Cruz), mouse anti-390 NLRP3/NALP3 (1:400 in 5% BSA, Cryo-2, Adipogen) or rabbit-anti-MMP-7 (1:1 000, ab4044, both Abcam), washed with PBS tween 0.1%, followed by incubation with secondary antibodies in 5% NFDM (goat anti-rabbit IgG-HRP or goat anti-mouse HRP (Cell Signaling). Bands were imaged using ECL Plus Western Blotting Reagent (GE Healthcare) with HRP-linked anti-GAPDH (1:1 000, sc-25778, Santa Cruz) as loading control. Restore Western Blot Stripping Buffer (Pierce) was used as indicated. Bands were quantified by ImageJ.

Co-Immunoprecipitation

Nuclear fractions, extracted as previously described, were incubated with rabbit anti-ASC antibody (sc-22514-R, magnetic Dynabeads® Protein G (Life technologies), analyzed by SDS-PAGE with rabbit anti-ASC and mouse anti-NLRP3 (Cryo-2, Adipogen) primary antibodies (1:200-1:1000, 5%

BSA), followed by secondary anti-rabbit (Cell Signaling) or anti-mouse (DAKO) antibodies (1:4000, 5% NFDM).

Global Gene Expression

Total RNA was extracted from murine bladders in RLT buffer with 1% β-Mercaptoethanol after disruption in a tissue homogenizer (TissueLyser LT, Qiagen) using Precellys® Lysing kits (Bertin Technologies), with the RNeasy® Mini Kit (Qiagen), amplified using GeneChip 3'IVT Express Kit, hybridized onto Mouse Genome 430 PM array strips for 16 hours at 45° C., washed, stained and scanned using the Geneatlas system (all Affymetrix).

Transcriptomic data was normalized using Robust Multi Average implemented in the Partek Express Software (Partek). Fold change was calculated by comparing infected to uninfected mice of the same genetic background (cut off fold change >1.41). Heat-maps were constructed by Gitools 2.1.1 software. Differentially expressed genes and regulated pathways were analyzed by Ingenuity Pathway Analysis software (IPA, Ingenuity Systems, Qiagen). Qiagen's list of 84 key inflammasome genes was selected for analysis.

Quantitative RT-PCR

Complementary DNA was reverse-transcribed from 1 µg of mice total RNA using SuperScript™ III First-Strand Synthesis System for RT-PCR (Invitrogen), and quantified in real time using qSTAR qPCR primer pairs against *Mus musculus* Il1b and Mmp7 genes (#MP206724 and #MP207902, Origene) and QuantiTect® SYBR® Green PCR kits (Qiagen) on a Rotor Gene Q (Qiagen). qRT-PCR reactions were run in technical duplicates and gene expression was analyzed based on a standard curve for each primer pair.

In Vitro Proteolysis

Recombinant human IL-1β NLRP-3 or PYCARD (ASC) (280 ng, H00003553-P02, H00114548-P01 and H00029108-P01 respectively, Abnova) were incubated with recombinant active human MMP-7 (0.035 U, #444270 Merck Millipore) in MMP reaction buffer (20 mM Tris, pH 7.6, 5 mM $CaCl_2$, 0.1 M NaCl) at 37° C. until stopped with 100 mM DDT. Fragments were detected by Western blot, using rabbit anti-IL-1 beta (1:2 000, ab9722, Abcam), rabbit anti-TMS1 (ASC) (1:1 000, ab155970 or p9522-75, US Biological) and mouse anti-CIAS1/NLRP3 (1:500, ab17267, Abcam) or rabbit anti-NLRP3 (1:500, sc-66846, Santa Cruz).

siRNA Transfection

HTB-9 cells were transfected with PYCARD/ASC and NLRP3 specific siRNAs (0.09 µM, FlexiTube GeneSolution, #GS29108 and #GS114548, Qiagen) or with AllStars Negative Control siRNA (#SI03650318, Qiagen) using the HiPerFect Transfection Reagent (#301705, Qiagen) for 17 hours, then infected. Transfection efficiency was assessed by Western blotting (FIG. 5B).

PCR Analysis

MA4P7 promoter and promoter flanks were amplified in 10 different fragments by PCR using 15 ng of total human genomic DNA and suitable forward and reverse primers (http://primer3.ut.ee/). Thermal cycling conditions were as follows: 95° C. for 2 min, 35 cycles (95° C. for 30 s, 60° C. for 30 s and 72° C. for 40 s) and 72° C. for 5 min.

Electrophoretic Mobility Shift Assay (EMSA)

Amplified DNA sequences from the MMP7 promoter were used as probes and labelled with GelGreen (Biotium). Each reaction contained 3-5 µg of DNA probe with, 5 µg of nuclear extract from infected HTB-9 cells, or 0.2-0.65 µg recombinant ASC (ABnova, H00029108-P01) or NLRP-3 (Abnova, H00114548-P01) in binding buffer (100 mM Tris, 500 mM NaCl and 10 mM DTT, pH 7). For the band shift competition assay, 0.5-1 µg of rabbit anti-ASC (Santa Cruz, sc-22514-R) or 0.5 µg rabbit anti-NLRP3 (Cryo-2, Adipogen) antibodies were used. Binding reactions were incubated at 15° C. for 30 min, loaded 454 onto a 6% non-denaturing, non-reducing polyacrylamide gel and ran in a 50 mM Tris (pH 7), 0.38 M glycine, and 2 mM EDTA buffer at 100 V for 2-3 hours. Mouse IgG2A isotype control (R&D Systems, MAB003) was used as negative control antibody. Mouse IgG2A isotype control, bovine actin (Sigma, A3653) and recombinant MMP-7 (Merck Millipore, #444270) (0.25 µg each) were used as control for unspecific protein binding. Gels were imaged using the Bio-RAD ChemiDoc™ system.

Experimental Urinary Tract Infection

Mice were bred and housed in the specific pathogen-free MIG animal facilities (Lund, Sweden) with free access to food and water. Female C57BL/6 mice or Il1b$^{-/-}$ (Horai et al. Journal of Experimental medicine 1998:187(9):1463-75), Nlrp$^{-/-}$, Asc$^{-/-}$ (Mariathasan S, et al. *Nature*. 2006; 440 (7081):228-32), Tlr4$^{-/-}$ (Hoshino K, et al. *J. Immunol.* 1999; 162(7):3749-52), Casp1$^{-/-}$ (Mariathasan et al. Nature 2004: 430(6996):213-218), Irf$^{-/-}$ (Sato M, et al. *Immunity.* 2000; 13(4):539-48) or Mmp7$^{-/-}$ (Wilson et al. Proc. Natl Acad Sci USA 1997: 94(4): 1402-1407) mice were used at 9-15 weeks of age. The Il1b−/− mice have recently been shown to be functionally defective for IL-1α (Freigang et al. Nat. Immunol. 2013; 14(10):1045-1053). The Casp1$^{-/-}$ mice were also deficient for Caspase-II (Kayagaki et al. Nature 2011, 479 (7371):117-121).

Mice under Isofluorane anesthesia were intravesically infected ($10^8$ CFU in 0.1 ml) through a soft polyethylene catheter (outer diameter 0.61 mm; Clay Adams). Animals were sacrificed under anesthesia; kidneys and bladders were asceptically removed and in the case of bladders, macroscopic pathology was documented by photography. Tissues were fixed with 4% paraformaldehyde or frozen for sectioning and RNA extraction. Viable counts in homogenized tissues (Stomacher 80, Seward Medical) were determined on TSA (37° C., overnight). Urine samples were collected prior to and at regular times after infection and quantitatively cultured. Neutrophils in uncentrifuged urine were counted, using a hemocytometer.

Histology and Immunohistochemistry

Tissues were embedded in OCT and 5-µm-thick fresh cryosections on positively charged microscope slides (Superfrost/Plus; Thermo Fisher Scientific) were fixed with 4% paraformaldehyde or acetone-methanol (1:1). For hematoxylin/eosin or immunohistochemistry, sections were blocked and permeabilized (0.2% Triton X-100, 5% goat normal serum (DAKO) or 1% BSA (Sigma), stained (anti-neutrophil antibody [NIMP-R14] (ab2557, Abcam), polyclonal *E. coli* antibody (1:100, NB200-579 Novus Biologicals), rabbit anti-IL-1 beta (1:50, ab9722), anti-MMP-7 (1:100, ab4044), anti-ASC (TMS1) (1:100, ab155970, all Abcam) or anti-NLRP3 (1:40, sc66846 Santacruz) rabbit antibodies. Alexa 488 anti-rat IgG or anti-rabbit IgG and Alexa 568 anti-rabbit IgG were secondary antibodies and nuclei were counterstained with DAPI (0.05 mM). Imaging was by fluorescence microscopy (AX60, Olympus Optical). Richard-Allan Scientific Signature Series Hemotoxylin 7211 and Eosin-Y 7111 (Thermo Scientific) were used to counterstain the tissue sections.

Il1b and Mmp7 Therapy

The IL-1 receptor antagonist, Anakinra (Kineret®, SOBI) or the broad-spectrum MMP inhibitor, Batimastat (ab142087, Abcam) were injected i.p.

Statistics

P-values <0.05 were considered significant. Prism version 6.02 (GraphPad), Mann-Whitney test (two tailed), One-way Anova (Kurkall-Wallis) and Two-way Anova non-matching test were used as appropriate.

Example 2

Acute Cystitis Strains Elicit an IL-1β Response in Human Bladder Epithelial Cells A mucosal cytokine response accompanies UTI and the epithelial cytokine repertoire includes IL-1β (Hedges et al. Interntional Journal of antimicrobial agents 1994; 4(2): 89-93). A functional role of IL-1β has not been characterized, however. To address this question, human bladder epithelial cells (HTB-9) were infected in vitro with E. coli strains causing acute cystitis. The uropathogenic E. coli (UPEC) strain CFT073 and the asymptomatic bacteriuria strain E. coli 83972 (ABU) were used as controls. Cells were infected with $10^8$ CFU/ml for 4 hours with gentamicin added after 1 hour, to focus on the early host response. Supernatants were collected for analysis in which inflammatory mediators in cell supernatants were quantified.

A rapid IL-1β response, indicated by IL-1β secretion was detected following infection with the acute cystitis (CY) strains CY-17, CY-92 and CY-132. E. coli CFT073 also triggered IL-1β secretion. In contrast, the response to the ABU strain E. coli 83972 was low (P<0.005 compared to uninfected cells), indicating a possible virulence-association (FIG. 1A). Pro-IL-1β and mature IL-1β were detected by Western blot analysis of the supernatants (FIG. 1B), suggesting that the acute cystitis strains activate de novo IL-1β synthesis and IL-1β processing. The IL-1β response was also shown to differ among the CY strains tested, with a low response to CY-49 (FIGS. 1A and 1B).

To address if IL-1β activation is a characteristic of acute cystitis strains, we infected human bladder epithelial cells with an epidemiologically defined collection of paediatric acute cystitis isolates (n=67). The majority of these strains (85%) triggered an IL-1β response >5 pg/ml and 64% of those triggered a high response (40-1,000 pg/ml, FIG. 1C). In contrast, a collection of paediatric ABU strains (n=66), obtained by screening of infants and children in the same geographic area and background population as the CY strains, did not trigger a strong IL-1β response (61%<5 pg/ml), resulting in significantly higher mean IL-1β concentrations for the CY than the ABU strains (121.8 and 32.4 pg/ml respectively, P<0.001, FIG. 1C). The results suggest that the majority of acute cystitis strains activate an IL-1β response in human bladder epithelial cells.

As pro-IL-1β is processed by the inflammasome, we examined if infection triggers an inflammasome response in human bladder epithelial cells. By confocal microscopy, we visualized the infection-induced changes in ASC (Apoptosis-associated speck-like protein containing a CARD), NLRP-3 (NACHT, LRR and PYD domains-containing protein 3), Caspase-1 and IL-1β levels (FIG. 1D). Inflammasome protein levels increased after infection with CY-92, CY-17, CY-132 and CFT073 but the ABU strain had no effect, consistent with the low IL-1β.

The results suggest that in addition to the IL-1β response, acute cystitis strains stimulate an inflammasome response in human bladder epithelial cells.

Example 3

In Vivo Control of Acute Cystitis by Il1b in the Murine UTI Model

The development of acute cystitis in mice after experimental infection with IL-1β inducing E. coli strains was examined. C57BL/6 WT mice were infected by intravesical inoculation with acute cystitis strains that triggered high IL-1β responses in human bladder epithelial cells, in vitro (CY-17 or CY-92) or with CFT073. Bladder infection was evaluated at sacrifice after 7 days (FIG. 2A) and the kinetics of infection were followed in urine samples obtained after 6 and 24 hours, 3 and 7 days (FIG. 2B).

Infected bladders showed macroscopic evidence of moderate inflammation, with an increase in size, edema and hyperaemia. Tissue pathology was confirmed by histology, with a loss of structure in infected mice, compared to uninfected controls (FIG. 2A). Tissue inflammation was accompanied by an increase in urine neutrophil numbers and bacterial numbers reached a peak after 24 hours and then declined (FIG. 2B). Bacteria and neutrophils were detected by immunohistochemistry in the bladder mucosa of infected mice (FIG. 2A) and a rapid IL-1β response, as confirmed by mucosal staining for IL-1β after 24 hours and elevated IL-1β levels in urine.

The role of IL-1β for the inflammatory response was then addressed, by infecting Il1b−/− mice with CFT073. The Il1b−/− mice were protected from bladder pathology, had lower bacterial counts and fewer infiltrating neutrophils than the C57BL/6 WT mice (FIG. 2C, P<0.001). Bladder morphology was intact and immunohistochemistry confirmed the low bacterial counts and the near absence of inflammatory cells in the tissues (FIG. 2D). The results demonstrate that clinical CY isolates cause acute cystitis in the mouse, characterized by a self-limiting inflammatory response and controlled by IL-1β.

Example 4

Hyper-Activation of IL-1β in Mice Lacking ASC or NLRP-3

To inactivate the inflammasome-dependent processing of IL-1β, subsequently infected NLRP-3 (Nlrp3$^{-/-}$), ASC (Asc$^{-/-}$) or Caspase-1 (Casp1$^{-/-}$) deficient mice, as described above. C57BL/6 WT mice were included as controls. Major, genotype-specific differences in bladder pathology were detected after seven days (FIGS. 2C and 2D). Bladders from Asc$^{-/-}$ and Nlrp3$^{-/-}$ mice were severely inflamed and enlarged with edema, hyperaemia and thickened bladder walls. By histology, most bladders from Asc$^{-/-}$ mice showed extensive loss of tissue structure with round cell infiltration and hypertrophy of the bladder epithelium (10/14 mice, 71%). Similar tissue destruction was observed in bladders from Nlrp3$^{-/-}$ mice (7/11 mice, 169 64%), (FIG. 2D).

Bladder pathology was accompanied by high bacterial 170 counts in urine and bladder tissue (FIG. 2C). In Asc$^{-/-}$ mice, the neutrophil influx accelerated until day 7, indicating a loss of homeostatic control and progression to chronic inflammation. Infiltrating bacteria and neutrophil aggregates or micro-abscesses were detected in the mucosa of Asc$^{-/-}$ and Nlrp3$^{-/-}$ mice, with extensive sloughing of epithelial cells into the lumen (FIG. 2D). Infection was accompanied by strong epithelial IL-1β staining in bladder tissue sections after 24 hours and elevated urine IL-1β levels. This hyper-inflammatory phenotype was recreated in Asc$^{-/-}$ mice after infection with the acute cystitis strains CY-92 and CY-17, which triggered high IL-1β responses in vitro.

Example 5

Tissue Retention of IL-1β and Bacterial Persistence in Casp1−/− Mice

In contrast, to Asc$^{-/-}$ and Nlrp3$^{-/-}$ mice, Casp1$^{-/-}$ mice were persistently infected but did not develop acute bladder pathology. Neutrophils were not retained in bladder tissues but were elevated in urine, suggesting that Casp1$^{-/-}$ mice fail to generate an environment suitable for tissue neutrophil retention. Furthermore, bacteria were present in urine but were not detected in the tissue sections. Accumulation of IL-1β Casp1$^{-/-}$ mice and low urine IL-1β confirmed the importance of Caspase-1 for IL-1β secretion (FIG. 4F). The elevated bacterial numbers in Casp1$^{-/-}$, Asc$^{-/-}$ and Nlrp3$^{-/-}$ mice, compared to WT mice suggested that a functional inflammasome is essential for bacterial clearance from infected bladders.

These studies are the first to reproduce essential aspects of acute cystitis in an animal model and to define acute cystitis as an IL-1β-dependent inflammatory state. Importantly, mice lacking functional ASC or NLRP-3 developed a hyper-inflammatory state with extensive tissue damage. This gives rise to the therapeutic use of these proteins in the prevention or treatment of cystitis.

Example 6

Gene Expression in Infected Bladders

To further characterize the molecular basis of bladder pathology, whole bladder RNA was subjected to genome-wide transcriptomic analysis. Regulated genes were defined in comparison with RNA from uninfected bladders of each genetic background (fold change (FC)>1.41, and P<0.05, FIG. 3A-D).

About 1800 genes were altered exclusively in mice with bladder pathology (heat map in FIG. 3A, histogram in FIG. 3B and Venn diagram in FIG. 3C). Genes with a FC>100 included metalloproteinase Mmp7, the neutrophil chemoattractants Cxcl1 and Cxcl6, the interferon-induced protein Ifit1 and calprotectine S100a8. By canonical pathway analysis, significantly regulated genes were shown to control granulocyte and leucocyte diapedesis and signaling, dendritic cell maturation, TNFR1 and 2-, NF-kB-, IL-6- and IL-10 signaling. These pathways were not significantly regulated in Il1b$^{-/-}$ or control mice, suggesting a direct disease association.

To address the role of IL-1β and the inflammasome for bladder pathology, genes encoding inflammasome complex constituents, inflammasome activators or downstream effectors were selected for analysis. A marked difference was observed, between mice that developed acute cystitis and resistant mice (FIG. 3D). Pathology was associated with a drastic increase in overall gene expression in this family, and Cxcl1, Cxcl3, Il1b and Il33 expression was most strongly regulated (FC 10-200). In contrast, Il18 and the NLRP genes were not regulated. A weak response was observed for genes encoding ASC (Asc) and Caspase-1. Innate immune regulators were moderately enhanced, such as the NF-κB constituents, Myd88, Mapk11 and chemokines Ccl-7, -5 and -2 (FC about 2). Importantly, inflammasome gene expression was virtually absent in Il1b$^{-/-}$ mice further emphasizing the key role of IL-1β for bladder pathology.

Networks of IL-1β dependent genes confirmed the overactivation of IL-1β dependent gene expression in Asc$^{-/-}$ and Nlrp3$^{-/-}$ mice. In Il1b$^{-/-}$ mice, the IL-1β dependent signaling cascade was completely abrogated, suggesting a lack of alternative activation mechanisms. Remaining, IL-1β-independent activated genes included the transcription factor Irf3, which controls the innate immune response to kidney infection and is activated via TLR4, TICAM-1 (TRIF) and TICAM-2 (TRAM) rather than the MyD88 and NF-κB pathway (7). In addition, upregulation of genes related to the inflammasome pathway was observed in Il1b$^{-/-}$ mice (Cxcl3, Ccl12, Ccl5, Naip1, Chuk), suggesting that their activation is not dependent on IL-1β.

Example 7

Mechanism of Atypical IL-1b Processing

IL-1β processing was further examined in human bladder epithelial cells infected with acute cystitis strains CY-17, CY-132 and CY-49, which generated the strongest IL-1β response in the epidemiological survey ($10^5$ CFU/ml, 4 h). CFT073 and ABU were included as positive and negative controls.

Cell lysates and supernatants from infected cells were subjected to Western blot analysis, with antibodies specific for IL-1β. Two fragments of approximately 29 kDa and 16-18 kDa were detected, corresponding to the N-terminal pro-piece and mature IL-1β. In the presence of the Caspase-1 inhibitor Z-VAD, IL-1β processing was inhibited by about 20%, suggesting that most of the IL-1β processing is caspase-independent.

Transcriptomic analysis was used to identify the most strongly upregulated genes in mice with bladder pathology. The Mmp7 gene, which encodes the matrix metalloproteinase (MMP-7) was identified as the most strongly regulated gene in mice with pathology (FC>200) as shown by gene expression and RT-PCR (FIGS. 4A and 4B). High MMP-7 expression was also detected by immunohistochemistry in bladder tissue sections from mice that developed pathology (Asc$^{-/-}$ and Nlrp3$^{-/-}$ mice) (FIG. 4C) where staining was exclusively epithelial with shedding of MMP-7 positive epithelial celinto the bladder lumen. Epithelial MMP-7 activation was detected as early as 24 hours after infection but MMP-7 was not regulated in resistant mice (Il-1b$^{-/-}$ or Casp1$^{-/-}$ mice) (FIG. 4C) at 7 days. Increased Il1b and Mmp7 mRNA levels were confirmed by RT-PCR, in these tissues compared to WT mice.

MMP-7 was subsequently shown to cleave or degrade IL-1β, in vitro. GST-tagged recombinant IL-1β was incubated with purified MMP-7 and proteolytic fragments were identified by Western blots using IL-1β specific antibodies (FIG. 4D). Kinetic analysis showed a time-dependent cleavage of IL-1b with a gradual reduction in full-length protein from 10 to 60 minutes. After 24 hours, IL-1β was completely degraded by MMP-7 (FIG. 4D). Time-dependent ASC degradation by MMP-7 was also detected but NLRP-3 was not affected. The IL-1β degradation products corresponded approximately to pro-IL-1β (36 kDa), the N-terminal fragment (29 kDa) and mature IL-1β (16-18 kDa), also seen in supernatant from cells infected with CY-92. Addition bands were also detected after MMP-7 degradation (FIG. 4D). NLRp-3 was not degraded and therefore serves as a negative control for ASC degradation by MMP-7.

To further evaluate the involvement of MMP-7 in acute cystitis, Mmp7−/− mice were infected with CFT073. No disease phenotype was detected (FIG. 4E) and Il1b and IL-1β-dependent gene expression was comparable to WT mice. Activated genes were involved in IRF1-dependent IL-1 signaling, including Birc3, Myd88, Irf1 and Ccl5. A moderate IL-1β response was observed in these mice, with submucosal IL-1β staining and moderate mucosal accumulation (FIG. 4F). IL-1β levels in urine were comparable to those of WT and Casp1$^{-/-}$ mice (FIG. 4F).

The results identify an alternative MMP-7-dependent mechanism of pro-IL-1β processing in inflammasome-deficient Asc$^{-/-}$ and Nlrp3$^{-/-}$ mice.

Example 8

NLRP-3 and ASC Act as Negative Regulators of MMP7 Expression

To understand the mechanism of increased MMP-7 expression in infected Asc$^{-/-}$ and Nlrp3$^{-/-}$ mice, we examined if ASC and/or NLRP-3 may act as negative regulators of MMP7 expression. ASC or NLRP-3 expression was inhibited by transfection of human bladder epithelial cells with ASC- or NLRP3-specific siRNAs and the effects on MMP-7 expression were quantified by confocal imaging and Western blots. MMP-7 expression increased drastically in transfected and infected cells where the expression of ASC or NLRP-3 had been inhibited (FIGS. 5A and 5B). By co-immunoprecipitation, ASC was shown to pull down NLRP-3 in nuclear extracts of uninfected cells but after infection, a reduction in ASC/NLRP-3 interaction was detected suggesting that a loss of ASC/NLRP-3 interaction in the nuclear compartment accompanies MMP7 activation.

To determine if ASC and NLRP-3 interact with the MMP7 promoter, DNA fragments spanning the entire promoter were used as probes in electrophoretic mobility shift assays (EMSA). A DNA fragment of 259 bp, adjacent to the transcription start site (P1, position −18/−276) was shown to interact with a nuclear protein extract from infected bladder cells, resulting in a significant band shift (FIGS. 5C and 5D). Specificity for ASC and NLRP-3 was confirmed by competition with specific antibodies (FIG. 5D). In the absence of nuclear extract, the probe formed a single low molecular weight 256 band, serving as a negative control. To confirm that ASC binds directly to the MMP7 promoter, recombinant ASC protein was incubated with the 259 bp DNA sequence and examined by EMSA. Strong dose-dependent binding of ASC to MMP7 promoter DNA was detected as a band shift, which was competitively inhibited by specific antibodies (FIG. 5E).

The results suggest that NLRP-3 and ASC act as negative regulators of MMP7 expression and identify an ASC binding site in MMP7 promoter DNA, adjacent to the transcription start site.

Example 9

Therapeutic Intervention—Efficacy of the IL-1 Receptor Antagonist and MMP Inhibitor The results suggested that an exaggerated IL-1β response drives bladder pathology. To address this hypothesis, Asc$^{-/-}$ mice were treated with the IL-1 receptor antagonist Anakinra (IL-1RA), 30 minutes before infection and daily after infection with E. coli CFT073 (1 mg in 100 μl of PBS i.p. per mouse for seven days, FIG. 6A). A dramatic therapeutic effect of Anakinra was observed compared to untreated Asc$^{-/-}$ mice (FIG. 6B-D). Anakinra-treated mice were protected against macroscopic bladder pathology, edema and hyperemia (FIGS. 6B and 6C). A marked reduction in pathology was also observed in bladder tissue sections (FIG. 6D). The mucosal neutrophil infiltrate was prevented and mucosal integrity was maintained. Consistent with this reduction in inflammation, urine neutrophil numbers were low (FIG. 6E). Bacterial counts remained elevated however, suggesting a key role of IL-1 signaling for bacterial clearance (FIG. 6E).

To address the contribution of MMP-7 to pathology, Asc$^{-/-}$ mice were also treated with an MMP inhibitor (Batimastat), (0.5 mg in 100 μl of PBS i.p. 30 minutes before, first three and last three days of infection, FIG. 6A). Treated mice were protected against macroscopic bladder pathology (FIG. 6B) with a reduction in the bladder edema and hyperemia compared to untreated Asc$^{-/-}$ mice (FIG. 6C). Neutrophil infiltration was markedly reduced (FIG. 6D). By Western blot analysis of urine samples, mice treated with IL-1RA showed a loss of mature IL-1β in urine and mice treated with the MMP inhibitor showed defective processing of IL-1β. As in the IL-1RA-treated mice, bacterial numbers remained elevated in MMP1 treated mice (FIG. 6E). By immunohistochemistry, some retention of unprocessed IL-1β in bladder tissue was detected, consistent with the need for MMP-7 and IL-1R to secrete mature IL-1β.

These results suggest that the hyper-inflammatory state that causes acute cystitis can be attenuated by blocking the access of IL-1β to its receptor and by inhibiting MMP-7. Thus these molecules are functional targets for immune-modulatory therapy.

Example 10

IL-1β and MMP-7 Responses in Human Bladder Cells and Patients with Acute Cystitis To address if the IL-1β response of human bladder to infection with acute cystitis strains is accompanied by an increase in MMP-7 protein levels, extracts of human bladder cells were subjected to Western blot analysis. MMP-7 was detected in cells infected with the acute cystitis strains or CFT073 but not with the ABU strain. The results demonstrate that the human response to infection with acute cystitis strains includes IL-1β/MMP-7.

To further address the human relevance of the IL-1β/MMP-7 response, urine samples were obtained from patient with acute cystitis at the time of diagnosis. A diagnosis of acute cystitis was based on urgency, frequency and/or dysuria and a positive dipstick but no fever (n=9). Samples were also obtained from patients with ABU (n=31, who carried the prototype ABU strain E. coli 83972, following therapeutic inoculation.

By ELISA, elevated concentrations of urine IL-1β (>10 pg/ml) were detected in 9/9 patients with acute cystitis (FIG. 7A). The urine IL-1β response was significantly lower in patients with long-term ABU (P<0.001). The urine samples were also examined for the MMP-7 content (FIG. 7B). Samples positive for MMP-7 were found in both patient groups but the highest MMP-7 concentrations were present in the acute cystitis group (P<0.001).

The results show that patients with acute cystitis have elevated concentrations of IL-1β and MMP-7 in urine, identifying IL-1β and MMP-7 as biomarkers of acute cystitis.

Example 11

Different Genes Control the Susceptibility to Acute Cystitis and Acute Pyelonephritis The clinical entities of acute pyelonephritis an acute cystitis typically are quite distinct, suggesting a difference in molecular pathogenesis. To test this hypothesis, we examined the kidneys from infected Asc$^{-/-}$ and Nlrp3$^{-/-}$ mice. There was no evidence of macroscopic kidney pathology in the mice that developed severe acute cystitis and bacterial kidney counts were not elevated, compared to WT mice. Bacteria and scattered neutrophils were detected by immunohistochemistry, along the renal pelvic mucosa but the tissue structure was unaffected.

As Irf3 regulates the susceptibility to acute pyelonephritis, Irf3$^{-/-}$ mice were used as positive controls for kidney pathology. After infection, their kidneys were severely inflamed, with macroscopic abscesses. Bacterial counts and neutrophil numbers were elevated compared to WT mice. Neutrophil infiltration and bacterial invasion was detected in the mucosa and collecting ducts. There was, however, no evidence of bladder pathology in Irf3$^{-/-}$ mice. NLRP-3 and ASC staining resembled that in WT mice and the IL-1 β response was weak.

The results demonstrate that IL-1β and inflammasome genes do not control the susceptibility to acute pyelonephritis.

The invention claimed is:

1. A method for treating cystitis comprising administering to a patient in need thereof, an effective amount of a reagent selected from the group consisting of an interleukin-1 receptor antagonist and an MMP inhibitor.

2. The method of claim 1 wherein the cystitis is acute cystitis that is infection-induced.

3. The method of claim 1 wherein the reagent is an interleukin-1 receptor antagonist.

4. The method of claim 3 wherein the interleukin-1 receptor antagonist is anakinra.

5. The method of claim 1 wherein the reagent is an MMP inhibitor.

6. The method of claim 5 wherein the MMP inhibitor is an MMP7 inhibitor.

7. The method of claim 6 wherein the MMP7 inhibitor is Batimastat.

* * * * *